(12) United States Patent
Cosman

(10) Patent No.: US 10,363,063 B2
(45) Date of Patent: Jul. 30, 2019

(54) ELECTROSURGICAL SYSTEM

(71) Applicant: Cosman Medical Inc., Burlington, MA (US)

(72) Inventor: Eric Richard Cosman, Belmont, MA (US)

(73) Assignee: Cosman Medical Inc., Burlington, MA (US)

( * ) Notice: Subject to any disclaimer, the term of this patent is extended or adjusted under 35 U.S.C. 154(b) by 0 days.

(21) Appl. No.: 15/349,785

(22) Filed: Nov. 11, 2016

(65) Prior Publication Data

US 2017/0065342 A1    Mar. 9, 2017

Related U.S. Application Data

(63) Continuation of application No. 13/776,685, filed on Feb. 25, 2013, now abandoned.

(51) Int. Cl.
| | |
|---|---|
| *A61B 18/14* | (2006.01) |
| *A61B 18/12* | (2006.01) |
| *A61B 17/34* | (2006.01) |
| *A61N 1/05* | (2006.01) |
| *A61N 5/00* | (2006.01) |
| *A61B 18/18* | (2006.01) |
| *A61M 25/01* | (2006.01) |
| *A61M 25/06* | (2006.01) |
| *A61N 1/06* | (2006.01) |
| *A61N 1/36* | (2006.01) |
| *A61B 18/00* | (2006.01) |

(52) U.S. Cl.
CPC ...... *A61B 17/3415* (2013.01); *A61B 17/3401* (2013.01); *A61B 18/1206* (2013.01); *A61B 18/1492* (2013.01); *A61B 18/18* (2013.01); *A61M 25/0102* (2013.01); *A61M 25/065* (2013.01); *A61M 25/0662* (2013.01); *A61N 1/0551* (2013.01); *A61N 1/06* (2013.01); *A61N 1/36* (2013.01); *A61N 5/00* (2013.01); *A61B 2018/0044* (2013.01); *A61B 2018/00083* (2013.01); *A61B 2018/00577* (2013.01); *A61B 2018/00821* (2013.01); *A61B 2018/1435* (2013.01); *A61B 2218/002* (2013.01); *A61M 2025/0681* (2013.01)

(58) Field of Classification Search
CPC . A61B 18/1492; A61B 18/1206; A61B 18/18; A61B 2018/00083; A61B 2018/0044; A61B 2018/00577; A61B 2018/00821; A61B 2018/1435; A61B 2218/002; A61N 5/00; A61N 1/0551
USPC .......................................................... 607/46
See application file for complete search history.

(56) References Cited

U.S. PATENT DOCUMENTS

| | | | |
|---|---|---|---|
| 5,935,123 A | 8/1999 | Edwards et al. | |
| 6,565,562 B1 * | 5/2003 | Shah ................. | A61B 18/1492 128/898 |
| 7,862,563 B1 * | 1/2011 | Cosman ............ | A61B 18/1477 606/41 |
| 2002/0077683 A1 | 6/2002 | Westlund et al. | |
| 2004/0064173 A1 * | 4/2004 | Hine .................... | A61N 1/056 607/122 |
| 2004/0147963 A1 | 7/2004 | Sommer et al. | |
| 2004/0210290 A1 | 10/2004 | Omar-Pasha | |
| 2006/0173407 A1 | 8/2006 | Shaughnessy et al. | |

(Continued)

*Primary Examiner* — Carl H Layno
*Assistant Examiner* — Erin M Piateski

(57) ABSTRACT

A system and method involving an electrode system can include a flexible shaft.

17 Claims, 11 Drawing Sheets

(56) References Cited

U.S. PATENT DOCUMENTS

| | | |
|---|---|---|
| 2006/0178666 A1 | 8/2006 | Cosman |
| 2012/0089123 A1* | 4/2012 | Organ .................... A61B 5/01 |
| | | 604/523 |
| 2012/0185022 A1 | 7/2012 | Noda et al. |

* cited by examiner

ELECTROSURGICAL SYSTEM

CROSS-REFERENCE TO RELATED APPLICATION

This application is a continuation of U.S. application Ser. No. 13/776,685, entitled "Electrosurgical System", filed Feb. 25, 2013, abandoned Jul. 28, 2017, which is incorporated by reference in its entirety.

TECHNICAL FIELD

This invention relates generally to epidural field therapy.

BACKGROUND

The use of radio frequency (RF) generators and electrodes to be applied to tissue for pain relief or functional modification is well known. For example, the RFG-3B RF lesion generator of Radionics Inc., Burlington, Mass. and its associated electrodes enable electrode placement of the electrode near target tissue and heating of the target tissue by RF power dissipation of the RF signal output in the target tissue. For example, the G4 generator of Cosman Medical, Inc. Burlington, Mass. and its associated electrodes such as the Cosman CSK, and cannula such as the Cosman CC and RFK cannula, enable electrode placement of the electrode near target tissue and heating of the target tissue by RF power dissipation of the RF signal output in the target tissue. Temperature monitoring of the target tissue by a temperature sensor in the electrode can control the process. Heat lessons with target tissue temperatures of 60 to 95 degrees Celsius are common. Tissue dies by heating above about 45 degrees Celsius, so this process produces the RF heat lesion. RF generator output is also applied using a pulsed RF method, whereby RF output is applied to tissue intermittently such that tissue is exposed to high electrical fields and average tissue temperature are lower, for example 42 degrees Celsius or less.

RF generators and electrodes are used to treat pain and other diseases. Examples are the equipment and applications of Cosman Medical, Inc., Burlington, Mass. such as the G4 radiofrequency generator, the CSK electrode, CC cannula, and DGP-PM ground pad. Related information is given in the paper by Cosman E R and Cosman B J, "Methods of Making Nervous System Lesions", in Wilkins R H, Rengachary S (eds.); Neurosurgery, New York, McGraw Hill, Vol. 3, 2490-2498; and is hereby incorporated by reference in its entirety. Related information is given in the book chapter by Cosman E R Sr and Cosman E R Jr. entitled "Radiofrequency Lesions.", in Andres M. Lozano, Philip L. Gildenberg, and Ronald R. Tasker, eds., Textbook of Stereotactic and Functional Neurosurgery (2nd Edition), 2009, and is hereby incorporated by reference in its entirety.

The Cosman CC cannula and RFK cannula, manufactured by Cosman Medical, Inc. in Burlington, Mass., include each an insulated cannula having a pointed metal shaft that is insulated except for an uninsulated electrode tip. The cannula has a hub at its proximal end having a luer fitting to accommodate a separate thermocouple (TC) electrode, for example the Cosman CSK electrode, Cosman TCD electrode, and Cosman TCN electrode, that can deliver electrical signal output such as RF voltage or stimulation to the uninsulated electrode tip. The Cosman CSK and TCD electrodes have a shaft that is stainless steel. The Cosman TCN electrode has a shaft that is Nitinol. A disadvantage of this system is that fluid injection into the cannula cannot be achieved when the TC electrode is also in the cannula. Another disadvantage is that the temperature sensor probe and the cannula are separate elements, which increases the complexity of the components needed for the system. Another disadvantage of the Cosman CC and RFK cannula is that its shaft is constructed from stainless steel hypotube. Another disadvantage of the Cosman CC and RFK cannula is its shaft is not flexible enough for epidural placement. Related information is given in Cosman Medical brochure "Four Electrode RF Generator", brochure number 11682 rev A, copyright 2010, Cosman Medical, Inc., and is hereby incorporated by reference herein it its entirety.

Each injection electrode made by Cosman Medical Inc. (Burlington, Mass.), including the CU electrode, the CR electrode, and the CP electrode models, has a shaft including metal tubing with sharp distal end for insertion into tissue to reach a spinal target. The shafts of the Cosman injection electrodes have lengths 6 cm (2.4 inches), 10 cm (3.9 inches), or 15 cm (5.9 inches). The shaft of a Cosman injection electrode is configured to penetrate the skin surface, muscle, and other tough bodily tissues to enable percutaneous placement of the electrode tip at nerves outside and around the bony spinal column. The shaft of a Cosman injection electrode is insulated except for an exposed conductive tip portion and has an electrical connection to a signal generator for delivery of stimulation or RF signal outputs to the target tissue. Each has a flexible injection tube and a port to allow injection of contrast, anaesthetic, or saline solution fluid to the target tissue. The CU electrode incorporates a temperature sensor positioned within the exposed, conductive tip portion. The CR and CP electrodes do not incorporate a temperature sensor. The CP electrode can be used to effect a stimulation-guided nerve block, whereby an electrical stimulation signal is applied to the CP electrode via its electrical connector, stimulation signals are applied to nerve tissue nearby the conductive tip of the CP electrode, and anesthetic fluid is injected through the CP shaft once desired stimulation response is achieved by positioning of the exposed tip. The CR electrode can be used to effect a stimulation-guided RF therapy without temperature control, whereby an electrical stimulation signal is applied to the CR electrode via its electrical connector, the stimulation signal is applied to nerve tissue nearby the conductive tip of the CR electrode in order to position the exposed tip of the electrode near target nerves, RF generator output is applied to the CR electrode via the same electrical connector, RF output is applied to tissue nearby the exposed tip of the electrode without temperature monitoring. The CR electrode can also be used to effect non-stimulation-guided RF therapy, whereby stimulation guidance is not utilized. The CU electrode can be used to effect a stimulation-guided RF therapy with temperature monitoring and control, whereby an electrical stimulation signal is applied to tissue via the CU electrode to position its exposed tip near target nerves, and RF output is applied to tissue near the exposed tip to effect medical treatment. The CU electrode can also be used to effect non-stimulation-guided RF therapy, whereby stimulation guidance is not utilized. The Cosman injection electrodes are not configured to be positioned by the epidural space. The shafts of the Cosman injection electrodes are not substantially flexible. The lengths of the Cosman injection electrodes' shafts are less than 5.9 inches. The Cosman injection electrodes are not structed using a spring coil. The Cosman injection electrodes are not introduced into the human body via an introducer needle, such as an epidural needle. Related information is given in Cosman Medical brochure "Four Electrode RF Generator", brochure number 11682 rev A, copyright 2010, Cosman Medical, Inc., and is hereby incorporated by reference herein in its entirety.

In one embodiment, U.S. Pat. No. 7,862,563 by E R Cosman Sr and E R Cosman Jr presents a unitized injection electrode with an electrically-insulated shaft, an exposed metallic tip, a temperature sensor within the exposed metallic tip, cables that connect to the electrode via a single, flexible leader connector that splits into two parts of which the first is terminated by a connector configured to carry high-frequency and stimulation signals and temperature-measurement signals, and the second is terminated by an injection port through which fluid can be injected into the shaft and out the distal end of the electrode. One limitation of this prior art is that it does not show a unitized injection electrode for which the metallic tip and insulated shaft are constructed using a spring coil and a central stiffening wire. One limitation of this prior art is that it does not show the application of a unitized injection electrode in the epidural space.

In the prior art, the Cosman TEW electrode system includes an electrode with a spring-coil tip that has a temperature sensor at its distal closed end. The TEW electrode is introduced into the human body by means of an insulated cannula. The TEW electrode is designed for RF treatment of the trigeminal facial nerve via the foremen ovale of the human skull. The TEW electrode is not electrically insulated. The shaft of the TEW electrode is a metallic tube to the distance end of which is attached a spring coil. The coil tip of the TEW electrode is configured to emerge from the end of the cannula and into the body without diverging substantially from its predetermined curve. The TEW electrode's spring coil is no longer than 0.33 inches. The TEW electrode's spring coil emerges from the distal end of the cannula by no more than 0.33 inches. The TEW electrode is not configured to be threaded through the epidural space. The TEW electrode is not configured to be threaded through 12 inches to 34 inches of the epidural space. The TEW electrode is not long enough to apply RF therapy to multiple spinal nerves via a single skin puncture and the epidural space. The TEW electrode does not have an injection port. The TEW electrode is not configured to allow for outflow of fluids from its spring coil tip. Related information is given in Cosman Medical brochure "Four Electrode RF Generator", brochure number 11682 rev A, copyright 2010, Cosman Medical Inc., and is thereby incorporated by reference herein in its entirety.

The Cosman Flextrode RF electrode system includes an electrode and an introducer cannula. The flextrode electrode's shaft is approximately 15 cm (5.9 inches) in length and is constructed from a metal tube whose distal end has a spiral cut over the distal 1.25 inches. A temperature sensor is located at the distal, closed end of the shaft. The electrode is induced into the human body via the introducer cannula which has a sharped distal end and whose shaft is electrically insulated. When the electrode is introduced through the cannula, 11 mm of the electrode extends beyond the cannulas distal end into the tissue. The Flextrode electrode is not electrically insulated. RF energy is applied to the tissue by the length of the Flextrode electrode that extends beyond the cannula's distal tip and the uninsulated distal tip of the cannula. The Flextrode is configured to penetrate tissue, such as the fibrous tissue of the intervertebral disc, where it emerges from the distal end of the cannula. The Flextrode's stiffness is configured so that its tip can move through the curved tip of the introducer cannula but remain substantially straight as it penetrates tissue. The Flextrode electrode is not configured for placement in the epidural space. The Flextrode is not configured for injection of fluids into the human body. Related information is given in Cosman Medical brochure "Four Electrode RF Generator", brochure number 11682 rev A, copyright 2010, Cosman Medical Inc., and is hereby incorporated by reference herein in its entirety.

The Radionics DiscTrode RF electrode system includes an electrode and an introducer cannula. The disctrode electrode's shaft is approximately 9 inches in length and is constructed from a metal tube whose distal end has thin cuts over the distal 2.5 inches. A temperature sensor is located at the distal, closed end of the shaft. The electrode is induced into the human body via the introducer cannula which has a sharped distal end and whose shaft is electrically insulated. When the electrode is introduced through the cannula, 5 cm (2 inches) of the electrode extends beyond the cannula's distal end into the tissue. The disctrode electrode is not electrically insulated. RF energy is applied to the tissue by the length of the disctrode electrode that extends beyond the cannula's distal tip and the uninsulated distal tip of the cannula. The disctrode is configured to penetrate tissue, such as the fibrous tissue of the intervertebral disc, where it emerges from the distal end of the cannula. The disctrode's stillness is configured so that its tip can move through the curved tip of the introducer cannula but remain substantially straight as it penetrates tissue. The disctrode electrode is not configured for placement in the epidural space. The disctrode is not configured for injection of fluids into the human body. Related information is given in an article by P M Finch entitled "The Use of Radiofrequency Heat Lesions in the Treatment of Lumbar Discogenic Pain", Pain Practice, Volume 2, Number 3, 2002, pages 235-240, which is here incorporated by reference herein in its entirety.

The Oratec Spinecath system includes a catheter and an introducer cannula. The catheter's shaft consists of a resistive coil that is entirely covered by electrical insulation. RF energy applied to the coil heats the internal resistive coil and tissue is heated by thermal conduction. RF energy is not applied to the tissue. A temperature sensor is located in the spinecath catheter. The electrode is induced into the human body via the introducer cannula which has a sharped distal end. The spinecath emerges from the distal end of the cannula by approximately 5 cm (2 inches). The spinecath catheter is not configured for placement in the epidural space. The spinecath is not configured for injection of fluids into the human body. Related information is given in an article by PM Finch entitled "The Use of Radiofrequency Heat Lesions in the Treatment of Lumbar Discogenic Pain", Pain Practice, Volume 2, Number 3, 2002, pages 235-240, which is here incorporated by reference herein in its entirety.

The use of catheters in the epidural space to treat pain is well known. A flexible catheter is introduced into the epidural space through an epidural needle inserted percutaneously through the sacral hiatus, through an intervertebral foramina, or through vertebral interspaces. An injection adaptor, such as a tuohy-borst adaptor, can be attached to the proximal end of the catheter to provide for the injection of fluids into the proximal end of the catheter that outflow into patient anatomy through the distal end of the catheter. Techniques such as lysis of adhesions, chemical neurolysis of nerve roots, and other medial methods are well known. Examples of epidural catheters include the Tun-L-XL catheter manufactured by EpiMed International, Farmers Branch, Tex. The Tun-L-XL catheter comprises a stainless steel spring coil whose distal end is welded into a ball, and which is covered by a plastic tube over its entire length except for the distal end. The coil wire is closely coiled except for a region of the exposed, distal coil where the cool loops are loosely wound to provide for preferential outflow of injected fluids. The coil can have a metal safety strap welded at the proximal and distal end of the coil. A stylet comprising a metal wire and a plastic hub attached to the proximal end of the wire, is inserted into the proximal end of the catheter to stiffen it. The stylet is removed, an injection adaptor is attached to the proximal end of the catheter, and fluids can be injected. Nerve stimulation signals can be delivered through the exposed metallic tip of the catheter by connecting the proximal end of the stylet to the output of a nerve stimulator, perhaps by means of an alligator clip, while the stylet is positioned inside the catheter. Related information is in "Epidural Lysis of Adhesions and Percutaneous Neuroplasty" by Gabor B. Racz, Miles R. Day, James E. Heavner, Jeffrey P. Smith, Jared Scott, Carl E. Noe, Laslo Nagy and Hana Ilner (2012), in the book "Pain Management—Current Issues and Opinions", Dr. Gabor Racz (Ed.), ISBN: 978-953-307-813-7, InTech, and is hereby incorporated by reference in its entirety. One disadvantage of the prior art in epidural catheters is that an electrode with a temperature monitoring is not used as a stylet. One disadvantage of the prior art in epidural catheters is that the stylet does not have an integrated connection cable to an electrical generator. One limitation of the prior art in epidural catheters is that electrical stimulation cannot be applied at the same time that fluid is injected through the catheter. One limitation of the prior an in epidural catheters is that prior catheters do not provided for temperature-controlled RF lesioning. One limitation of the prior art in epidural catheters is prior catheter systems have multiple pieces. One limitation of the prior art in epidural catheters is prior catheter systems are not a unitized injection electrode.

U.S. Pat. No. 6,246,912 by M E Sluijter, W J Rittman, and E R Cosman presents in FIG. 9 a catheter electrode with one or more electrical contacts, where the catheter electrode is placed in the epidural space and applies high frequency signals via its electrical contacts. The electrical contact are tubular rings bonded to the substrate catheter and connected to wires internal to the catheter. The catheter may have reinforced metal spirals in its construction. The catheter electrode does not provide for the injection of fluids. The catheter electrode does not apply high frequency signals to the tissue by the same spring coil that is part of its shaft construction.

U.S. Pat. No. 8,075,556 by A Betts presents a specific construction of a device configured for placement in the spinal canal and delivery of RF energy. Betts describes a catheter delivery device to transmit radiofrequency energy to a spinal canal, comprising: a needle having an open proximal end and an open distal end, and a lumen that extends from the open proximal end to the open distal end; a catheter having a blunt, metallic tip on a distal end of the catheter that transmits a radio frequency energy to the treatment site, wherein the catheter is telescopically disposed within the needle lumen to allow the tip to be maneuverably positioned within the spinal canal; a catheter hub coupled to a proximal end of the catheter a metallic wire element telescopically disposed within a lumen of the catheter; and an adapter hub coupled to a proximal end of the wire element, wherein the adapter hub is cooperatively engageable to the catheter hub to form a single shaft, wherein a proximal end of the adapter hub is configured couple to a radio frequency generating device, and wherein the adapter hub and the catheter hub are sized and dimensioned relative to one another such that engagement of the adapter hub to the catheter hub allows a distal end of the wire element to touch a seating surface of the tip such that the wire element delivers a radio frequency energy from the radio frequency generating device to the tip. A disadvantage of the prior art in Betts is that the catheter has an adaptor hub. A disadvantage of the system described in Betts is that a standard epidural catheter is not used. A disadvantage of the system described in Betts is that construction of the catheter using a metal coil is not described. A disadvantage of the system described in Betts is that a safety strap within the catheter shaft is not described; a disadvantage of the absence of a metallic safety strip is that the impedance of the catheter shaft can distort and/or diminish electrical signals conducted along the shaft. A disadvantage of the system described in Betts is that RF is not delivered without seating of the RF wire in the inner surface of the distal end of the catheter. A disadvantage of the system described in Betts is that the system does not provide temperature monitoring. A disadvantage of the system described in Betts is that the system does not provide for temperature-monitored RF therapy delivered through the catheter. A disadvantage of the system described in Betts is that the RF wire does include a temperature sensor. A disadvantage of the system described in Betts is that it not a unitized injection electrode. A disadvantage of the system described in Betts is that the RF wire is separate from the catheter. A disadvantage of the system described in Betts is that injection through the catheter cannot be effected while the RF wire is in place within the catheter. A disadvantage of the system described in Betts is that it does not provide for simultaneous injection of fluids and delivery of electrical signals.

U.S. patent application 2004/0210290 by Omar-Pasha describes a catheter electrode for pulsed RF treatment of nerves in the epidural space. One limitation of this prior art is that does not describe the use of a coil to construct the catheter electrode. Another limitation of this prior art is it does not describe an RF electrode system in which an RF electrode stylet is inserted into a standard epidural catheter.

The pulsetrode electrode manufactured by BioAmpere Research SRL, Verona, Italy is a flexible electrode comprising a plastic shaft, three ring electrodes near its distal end, a hub, an injection port connected to a tube that is connected directly to the hub, a generator wire that connects directly to the hub, a moveable stylet is inserted into the injection port and travels along the shaft of the electrode. The pulsetrode is configured for placement in the epidural space and delivery of radiofrequency fields to anatomy. Related information given in Bioampere Research brochure "Pulserode" and is hereby incorporated by reference herein in its entirety. One limitation of this prior art is that does not describe the use of a coil to construct the catheter electrode. Another limitation of this prior art is it does not describe an RF electrode system in which an RF electrode stylet is inserted into a standard epidural catheter. Another limitation of this prior art is that the distal end of the electrode is electrically insulated. Another limitation of the this prior art is that the active tip is not the sole active tip.

SUMMARY

The present invention relates to a system and method involving an electrode system having a flexible shaft. In one aspect, the present invention relates to a system involving a radiofrequency electrode configured for placement within the epidural space. In one aspect, the present invention relates to a flexible electrode that provides for stimulation-guidance and the injection of fluids into the epidural space. In one aspect, the present invention relates to a system for performing epidural pulsed RF using stimulation guidance and guidance by means of injection of radiocontrast agents from the active tip of the electrode. In one aspect, the present invention relates to a method for construction of an epidural electrode system. In one aspect, the present invention relates to the construction of an epidural electrode using metal coil over the proximal end of which insulation is positioned. In one aspect, the present invention relates to a one-piece electrode system with flexible shaft, and injection port, and a generator connector.

In one example, the epidural electrode system consists of a one-piece (also known as "unitized") electrode with an injection port and generator connection, that is introduced percutaneously through an epidural needle. The electrode conducts electrical signals, such as RF and pulsed RF signals to tissue in contact with the electrode's active tip, when the electrode is energized by an electrical power supply, such as a radiofrequency generator. In a more specific example, the electrode includes a temperature sensor within is active tip to provide temperature monitoring during the delivery of electrical signal, for example to provide for temperature-controlled RF pain treatment.

In one example, the one-piece, electrode's shaft is constructed using a spring coil whose proximal end is covered by an electrically-insulated sheath, and whose distal end is closed by a weld that incorporates the spring coil, any internal RF wires, any internal thermocouple wires, and internal structuring wires, such as a safety strap or fixed stylet. One advantage of this example is ease of manufacturing.

In one example, the one-piece electrode's shaft is constructed using a spring coil whose proximal end is covered by an electrically-insulated sheath; whose distal end is closed by a weld that incorporates the spring coil, any internal RF wires, any internal thermocouple wires, and internal structuring wires, such as a safety strap; and into whose proximal end a separate moveable stylet is inserted. One advantage of this example is ease of manufacturing.

In one example, the epidural electrode system consists of a two-piece system including a catheter with metallic tip and a RF electrode configured to be placed within the inner lumen of the catheter. One advantage of this example, this that the RF electrode can both deliver RF to the catheter tip, monitor the temperature at the catheter tip, and provide variable stiffening of the catheter shaft and tip.

One advantage of using a coil to construct the shaft and tip of a unitized injection electrode is that the shaft is flexible. One advantage of flexible shaft and tip in unitized injection electrode is that the electrode can be placed in the epidural space of the human body. One advantage of an epidural unitized injection electrode system is that injection of fluids and delivery of electrical signals, such as RF, can be effected at the same time. Ease of manufacturing is one advantage of the method of constructing a unitized injection electrode system for epidural RF using a spring coil covered with an insulative sheath and terminated at this distal end by a weld joint that captures internal RF and thermocouple wires.

Ease of manufacturing is one ad vantage of an epidural catheter electrode system for which an RF electrode is used as a stylet for an epidural catheter.

DESCRIPTION OF DRAWINGS

Like reference symbols in the various drawings indicate like elements.

Figure 4A:
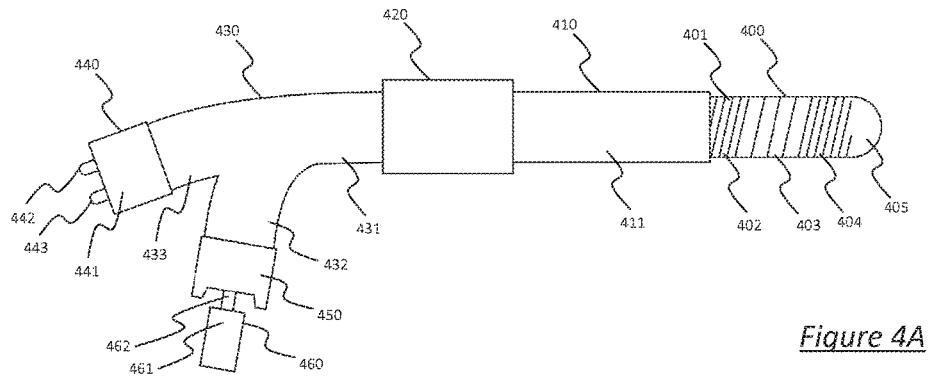
FIG. 4A is a schematic diagram showing connector in an external view a unitized injection electrode with a flexible active tip, a flexible shaft depicted in a straight position, an injection port, a generator connector, and a moveable stylet.
Figure 4B:
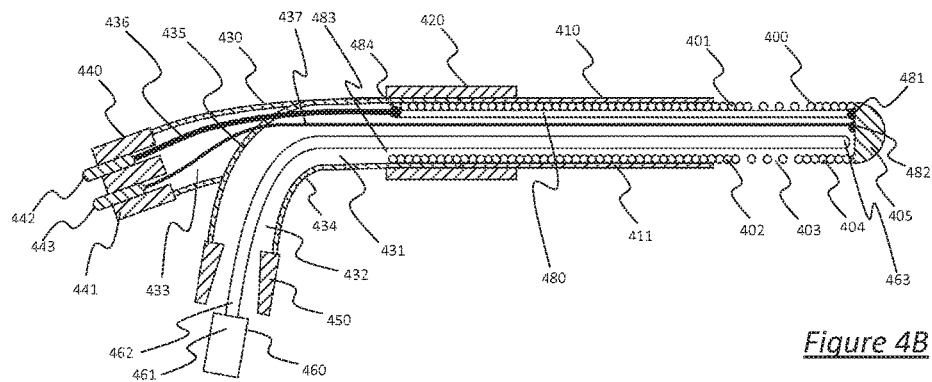
FIG. 4B is a schematic diagram showing in a section view a moveable stylet positioned inside a unitized injection electrode where a coil is used in the construction of the shaft and active tip, where the electrode has a temperature sensor, injection port, and a generator connector.

A reference to a figure by its numeric index alone is a reference to all figures having that numeric index as their prefex; for example, "FIG. 4" refers to FIG. 4A and FIG. 4B collectively.

DETAILED DESCRIPTION

Figure 1A:
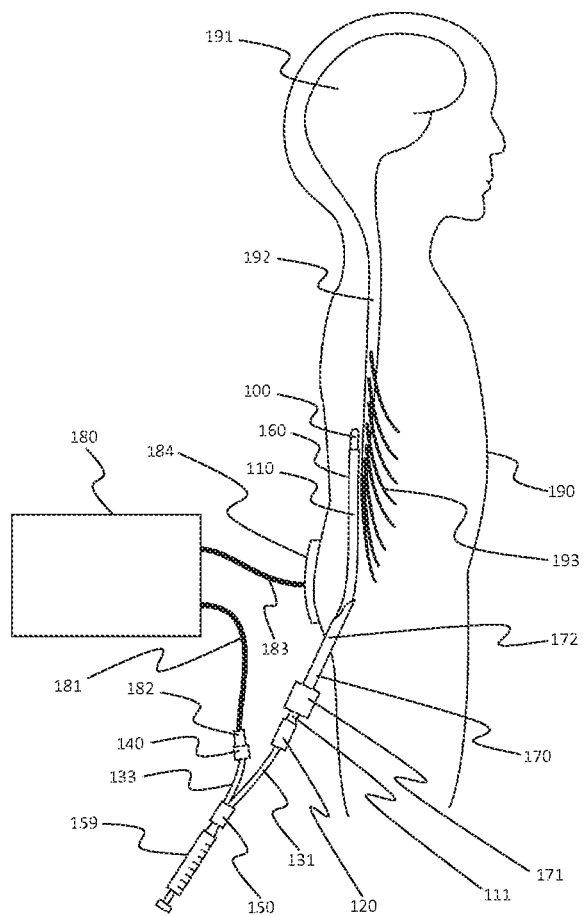
FIG. 1A is a schematic diagram showing a system including a catheter electrode wherein the electrode is placed in the epidural space and energized in a monopolar manner where a ground pad carries return currents from the electrode.

FIG. 1A presents an electrode system comprising injection electrode 160, introducer needle 170, ground pad 184, and generator 180, in accordance with one aspect of the present invention. Syringe 159 can be attached to port 150 of electrode 160 to provide for the injection of fluids into body 190 through electrode 160. In one embodiment, the system can provide for stimulation-guided epidural anesthesia and temperature-monitored radiofrequency treatment, include pulsed radiofrequency treatment, of nerves. In one embodiment, the system can provide for the application of high frequency electric fields to nerve by means of placing an electrode via the epidural space. In one embodiment, the system can provide for the application of high-frequency electric fields to nerve by means of placing an electrode via the neural foramina. In one embodiment, the system can provide for cost-effective manufacturing of a catheter electrode configured for placement in the epidural space. In one embodiment, the system can provide for cost-effective manufacturing of a temperature-monitoring catheter electrode configured for placement in the epidural space. In one embodiment, the system can provide for the construction of a catheter electrode capable of delivery of nerve stimulation signals, delivery of radiofrequency signals and fluid injection for medical procedures, such as pain management. In one embodiment, nerve stimulation signals produced by generator 180 can be used to position the electrode 160 for the purpose of an epidural anesthesia procedure, such as lysis of adhesions, chemical epidural necrolysis, epidural injection of alcohol, and epidural injection of phenol. In one embodiment, the electrode 160 can provide for the injection of fluids, such as radiocontrast agents, anesthetics, neurolytics agents, alcohol, phenol, saline, hyaluronidase, local anesthetic, corticosteroids, hypertonic saline. In one embodiment, the electrode tip 100 and shaft 110 can be visible in x-ray images, such as fluoroscopy. An advantage of this embodiment is that radiographic imaging can be used to position the electrode 160 in the human body 190. In one example, the system can be used to relieve pain. In one example, the system can be used to relieve pain by means of pulsed RF application to a dorsal root ganglion. In one example, the system can be used to relieve pain. In one example, the system can be used to relieve pain by means of pulsed RF application to spinal nerve. In one example, the system can be used to relieve pain due to cancer. In one example, the system can be used to relieve pain due to cancer by means of radiofrequency heat lesioning of a dossal nerve root. One advantage of the application of radiofrequency using an epidurally placed electrode is that nerve structures at multiple levels of the spine can be targeted by moving the epidural electrode through the epidural space.

Electrode 160 comprises active tip 100, shaft 110, proximal end of the shaft 111, hub 120, cable 131, injection port 150, generator cable 133, and generator connector 140. Introducer needle 170 comprises hub 171 and shaft 172. Generator 180 is connected to leader cable 181 and connector 182 to provide for connection to electrode connector 160. Generator 180 is connected to leader cable 183 and ground pad 184. Ground pad 184 is placed on the skin surface of human body 190. Human body 190 has brain 191, spinal cord 192, and spinal nerves 193. Electrode 160 is positioned in the human body 190. Electrode 160 enters the human body 190 by passing through needle 170. Generator 180 can generate an electrical potential between the ground pad 184 and the electrode 160, and thereby electrical current flows from the active tip 100 of the electrode 160, through the body 190, to the reference ground pad 184. In one example, electrode 160 is positioned in the epidural space in the human body 190. In one example, electrode 160 enters the epidural space via a median or paramedian approach. In one example, electrode 160 enters the epidural space via the sacral hiatus. In one example, electrode 160 enters the epidural space via an intervertebral foramina of the spinal column. In one example, the active tip 100 of the electrode 160 is positioned near a dorsal spinal nerve root. In one example, the active tip 100 of the electrode 160 is positioned near a dorsal root ganglion (DRG). In one example, the active tip 100 of the electrode 160 is positioned near a spinal nerve.

In one embodiment, the generator 180 is a medical radiofrequency generator. In one embodiment, the generator 180 provides for temperature-controlled radiofrequency and pulsed radiofrequency treatment of chronic pain. In one embodiment, the generator 180 is a high frequency electrical generator. In one embodiment, the generator 180 is nerve stimulator. In one embodiment, the generator 180 includes a temperature-measurement circuit.

In one embodiment, the needle 170 is an epidural needle. In one embodiment, the needle 170 is a tuohy needle. In one embodiment, the needle 170 has sigmoidal tip geometry, as shown in FIG. 1A. In one embodiment, the needle 170 is a spinal needle.

The electrode 160 can have one of a number of constructions accordance with the present invention. In one embodiment, electrode 160 has one of the constructions shown in FIG. 2, in one embodiment, electrode 160 has one of the constructions shown in FIG. 3. In one embodiment, electrode 160 has one of the constructions shown in FIG. 4. In one embodiment, electrode 160 has one of the constructions shown in FIG. 5. In one embodiment, electrode 160 has one of the constructions shown in FIG. 6. In one embodiment, electrode 160 has one of the constructions shown in FIG. 7. In one embodiment, electrode 160 has one of the constructions shown in FIG. 8, wherein cable 131 is omitted. In one embodiment, electrode 160 has one of the constructions shown in FIG. 8, wherein cable 131 is omitted and port 150 is omitted. The electrode 160 can be a unitized injection electrode. The electrode 160 can be a catheter into which a physically-separate electrode is inserted. The electrode 160 can be constructed using a spring coil. The electrode can include a temperature sensor, such as a thermocouple.

The electrode 160 can be configured for placement in the epidural space of a human body 190. The electrode can have a flexible shaft 110 and a tip 100. The tip 100 can be an uninsulated metallic coil, such as a round-wire spring coil, a flat-wire spring coil, a spiral cut metal tube, a laser-cut metal tube. The tip 100 can be stainless steel. The shaft 110 and tip 100 can include the same coil. The shaft 110 can be electrically insulated.

FIG. 1A shows one embodiment of cables for an injection electrode 160, wherein a root cable 131 provides a flow path for fluids injected into port 150 and housing for wires for generator connector 140, port 140 provides an opening for injection of fluids, and generator cable 133 carries wires from generator connector 150. In one embodiment, fluids injection into port 150 flow through the shaft 110 of the electrode and outflow into the body 190 through the tip 100. In one embodiment, port 150 is a luer port.

In one embodiment, needle hub 171 is a port, such as a luer port, through which fluids can be injected. In one embodiment, the needle shaft 172 is partially electrically-insulated with an metallic active tip and can be used as an RF cannula. In one embodiment, the needle 170 is an RF cannula.

Figure 1B:
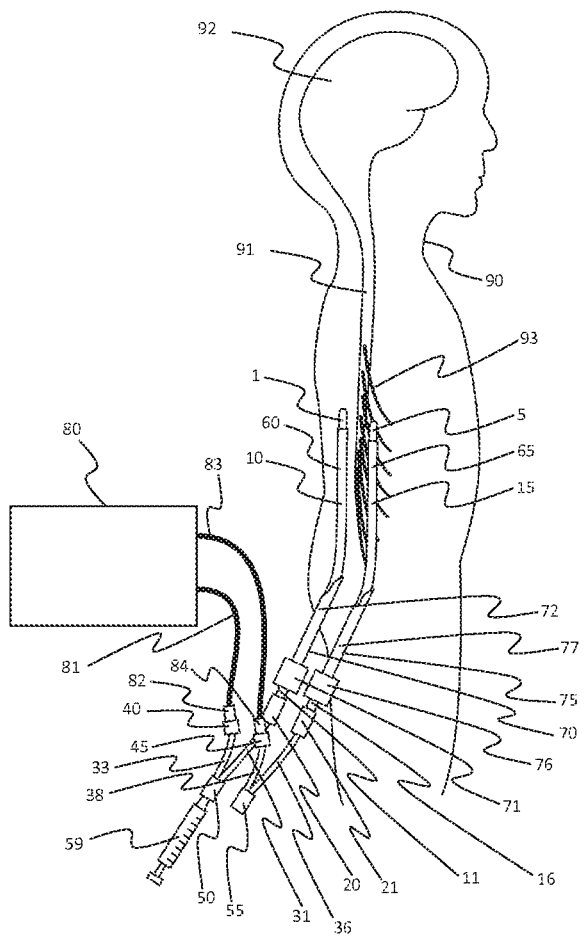
FIG. 1B is a schematic diagram showing a system including two catheter electrodes wherein the electrodes are placed in the epidural space and energized in a bipolar manner where current passes between electrodes.

FIG. 1B presents an electrode system comprising a first injection electrode 60, a second injection electrode 65, a first in introducer needle 70, a second introducer needle 75, and generator 180, in accordance with one aspect of the present invention. Syringe 59 can be attached to port 50 of electrode 60 to provide for the injection of fluids into body 90 through electrode 60.

Syringe 59 can be attached to port 55 of electrode 65 to provide for the injection of fluids into body 90 through electrode 65. Electrode 60 is introduced into the human body 90 through needle 70. Electrode 65 is introduced into the human body 90 through needle 75. In one embodiment electrode 60 can be equivalent to electrode 160 in FIG. 1A. In one embodiment electrode 65 can be equivalent to electrode 160 in FIG. 1A. In one example, Electrodes 60 and 65 can both be placed in the epidural space of the same human body at the same time, and electrodes 60 and 65 can be connected to opposite poles of the generator 180, and thereby be energized in a bipolar manner. An advantage of this configuration is that bipolar RF therapy can be effected in the epidural space of the human body 190.

Referring to FIG. 2, meaning FIGS. 2A, 2B, 2C, 2D, and 2E, in accordance with one aspect of the present, invention, a unitized injection electrode is presented that comprises an active tip 200, an electrically insulated shaft 210, a hub 220, cables 230, electrical signal connector 240, and injection port 250. The electrode can be constructed so that its active tip 200, insulated shaft 210, hub 220, cables 230, signal connector 240, and injection port 250 are inseparably connected. The distal end of the electrode is the end of the active tip 200, and the proximal end of the electrode is end of the cables 230. Electrode structures that are more distal are closer to the distal tip 205. Electrode structures that are more proximal are closer to the generator connector 240 and/or to the injection port 250.

The active tip 200 is constructed from coil 201 and closed distal end 205. The closed distal end 205 can be a weld, which can be formed by laser, electrical discharge, or other methods known to one skilled in the art. The closed 205 distal end can be formed with conductive glue. The closed distal end 205 can be created using solder. The close distal end can be formed using glue. The closed distal end 205 can be configured to be electrically conductive. The closed distal end 205 can be configured to be electrically connected to the coil 201. The tip 200 can be configured to deliver electrical signals, such as stimulation and RF signals, to tissue, such as nerves. The tip 200 can be configured to allow for the outflow of fluid. The tip 200 can be configured to allow for preferential outflow of fluid from one or more parts of the tip. In the embodiment presented in FIG. 2, the tip 200 has a proximal region 202 which is closely-coiled wire. The tip 200 has a middle region 203 in which the coils are separated to allow for fluid outflow. For example, the outflow region 203 can have a ratio between wire diameter and inter-wire spacing of 1:1. The tip 200 has a distal region 204 which is closely-coiled wire. It is understood one or more of the tip regions 202, 203, and 204 can be omitted in other embodiments of the electrode.

The closed distal end 205 can have the same outer diameter as the outer diameter of the rest of the active tip 200. The closed distal end 205 can be full radiused. The closed distal end 205 can be hemispherical. The closed distal end 205 can be flat. The closed distal end 205 can have a smaller diameter than the outer diameter of the rest of the active tip 200. The closed distal end 205 can have a larger diameter than the outer diameter of the rest of the active tip 200. In another embodiment of the present invention, the distal end 205 can be open; an advantage of this embodiment is that fluid can exit the electrode from the distal end.

The insulated shaft 210 is constructed of electrical insulation 211 that surrounds the coil 201 within it. The coil 201 within the shaft can be closely coiled wire like that of the proximal tip region 202. In one embodiment, the coil 201 can extend through the entire length of the shaft 210. In one embodiment, the coil 201 can extend only part of the length of the insulated shaft 210 and connect to another structure that has different flexibility, such as a tube or a spiral-cut tube. In one embodiment, the coil 201 can extend though the shaft 210 and the hub 220. In one embodiment, the coil 210 can extend though the shaft 210, the hub 220, and the cables 230.

The tip 200 and shaft 210 can be flexible. The tip 200 and shaft 210 can be configured for placement within the epidural space in the human body. The coil 201 can be a stainless steel spring coil. In one example, the coil 201 can be a spring coil used in the construction of epidural catheters, as is familiar to one skilled in the art of epidural anesthesia. The coil 201 can be constructed of wound round wire. The coil 201 can be constructed of wound flat wire. The coil 201 can be laser-cut tubing. The coil 201 can be laser-cut stainless-steel hypodermic tubing. The electrical insulation 211 can be constructed from one or more pieces and/or applications of medical grade plastic tubing, fluoropolymers, fluoroelastomers, silicone, polyester, polyolefin, polyimide, and other materials that are familiar to one skilled in the art of RF electrodes and epidural catheters. The electrical insulation 211 can be constructed from materials configured to produce shaft stiffness appropriate for epidural placement in the human body. The electrical insulation 211 can be a single a tube of fluoropolymer material, such as PTFE, FEP, ETFE, PET. The electrical insulation 211 can be heat shrink tubing that is shrunk over the coil 201. The electrical insulation 211 can be applied by coating the wire of the coil 201 before that wire is wound into the coil 201. The electrical insulation 211 can be PTFE heat shrink tubing that is shrunk over the coil 201. The electrical insulation 211 can be FEP heat shrink tubing that is shrunk over the coil 201. The electrical insulation 211 can be ETFE heat shrink tubing that it shrunk over the coil 201. The electrical insulation 211 can be PET heat shrink tubing that is shrunk over the coil 201. The electrical insulation 211 can consist of two layers of plastic material that surround the spring coil 201, as is familiar to one skilled in the art of epidural anesthesia catheters. The electrical insulation 211 can be produced by applying a layer of a first material to the coil, for example by spraying or painting, and then applying a second material, such as a tube, over the first material. The coil 201 can be wound wire of 0.004 inch diameter. The coil 201 can be wound wire of 0.005 inch diameter. The coil 201 can be wound wire of 0.006 inch diameter. The coil 201 can be wound wire of 0.007 inch diameter. The coil 201 can be wound wire of less than 0.004 inch diameter. The coil 201 can be wound wire of greater than 0.007 inch diameter. The outer diameter of the coil 201 can be in the range 21 gauge to 18 gauge. The outer diameter of the coil 201 can be smaller than 21 gauge. The outer diameter of the coil 201 can be larger than 18 gauge. The outer diameter of the coil 201 can be 20 gauge. The outer diameter of the coil 201 can be 19 gauge. The electrical insulation 211 can have wall thickness in the range 0.003 inches to 0.008 inches. The electrical insulation 211 can have wall thickness less than 0.003 inches. The electrical insulation 211 can have wall thickness greater than 0.008 inches. The electrical insulation 211 can have wall thickness 0.005 inches. The outflow section of the coil 203 can have spaces between adjacent coil loops that is substantially equal to the thickness of the wire from which the coil is wound. The outflow section of the coil 203 can have spaces between adjacent coil loops that is in the range 0.003 inches to 0.008 inches. The outflow section of the coil 203 can have spaces between adjacent coil loops that is less than 0.003 inches. The outflow section of the coil 203 can have spaces between adjacent coil loops that is greater than 0.008 inches. The outflow section of the coil 203 can have spaces between adjacent coil loops that is 0.005 inches. The outflow section of the coil 203 can have spaces between adjacent coil lops that is 0.006 inches. The length of the outflow section of the coil can be in the range 0.100 to 0.140 inches. The length of the outflow section of the coil can be less than 0100. The length of the outflow section of the coil can be greater than 0.140 inches. The length of the outflow section of the coil can be 0.120 inches.

In another embodiment of the electrode, more than one segment of insulation can be applied along the length of the electrode shaft, with bare coil 201 between each segment; an advantage of this embodiment is that RF energy can be applied to multiple separated tissue regions without applying RF energy directly to intervening regions. In another embodiment, a segment of insulation can cover closed end 205 and the distal end 204 of the tip 200. In another embodiment of the electrode, the insulation can be configured such that at one or more segments of the shaft, there is a gap in the insulation on one side of the shaft that exposes the underlying coil 201, and insulation covers the other opposite side of the coil; an advantage of this embodiment is that RF energy can be applied to tissue in contact with only one side of the electrode.

The tip 200 can have length between 2 mm and 60 mm. The tip 200 can be longer than 60 mm. The length of the active tip 200 can be 5 mm. The length of the active tip 200 can be 10 mm. The length of the active tip 200 can be 15 mm. The length of the active tip 200 can be 20 mm. The length of the active tip 200 can be 25 mm. The length of the active tip 200 can be 30 mm. The active tip 200 can have length configured to the application of RF signals to nerves for pain management. The active tip 200 can have length configured for epidural placement and injection of epidural anesthetics.

The length of the shaft 210 can be between 12 inches and 33 inches. The length of the shall 210 can be configured for epidural anesthesia procedures, as if familiar one skilled in the art. The length of the shaft 210 can be longer than 33 inches. The length of the shaft 210 can be shorter than 12 inches. The length of the shaft 210 can be 16 inches. The length of the shaft 210 can be configured to reach the L2 vertebral level percutaneously and epidurally via the sacral hiatus.

The hub 220 can have a diameter larger than the insulated shaft 210. The hub 220 can be configured to facilitate rotation of the electrode shaft 210 and tip 200. The hub 220 can be omitted and the cables 230 can connect directly to the shaft 210. The hub 220 can have similar outer dimension and aspect as tuohy-borst adaptors that are typically attached to the end of epidural catheters, as is familiar one skilled in the art. The hub 220 can have outer diameter in the range 0.250 inches to 0.500 inches. The hub 220 can have outer diameter less than 0.250 inches. The hub 220 can have outer diameter greater than 0.500 inches.

The cable 230 can be flexible. The cable 230 can be rigid. The cable 230 can have both rigid and flexible element. The cable 230 can have a hollow inner lumen capable of carrying injected fluids into the electrode shaft 210 and tip 200. The cable 230 can contain a tube capable of carrying wires for connection to the jacks on an RF generator. In one embodiment, the cables 230 can be construction from flexible tubes, glue, and wires for connection to the generator. In one embodiment, the cables 230 can be construction from flexible tubes, glue, a Y-splitter structure, and wires for connection to the generator. In one embodiment, the cable 230 can be constructed like the cable of the Cosman CU electrode, sold by Cosman Medical, Inc. In other embodiments, the cable can be constructed using the systems and methods presented in U.S. Pat. No. 7,862,663 by E R Cosman Sr and E R Cosman Jr. In the embodiment shown in FIG. 2, the cable 230 has a single root 231 that connects to the hub 220, a branch 232 that connects to and carries fluid from injection port 250, and a branch 233 that connects to and carries wires from the connector 240.

The electrical signal connector 240 can be configured to carry signals from an RF generator to the active tip 200 of the electrode, as is familiar to one skilled in the art. In one embodiment, the connector 240 can be configured to connect to a nerve stimulation device. The connector 240 can be configured to carry sensory nerve stimulation signals, motor nerve stimulation signals, thermal RF signals, pulsed RF signals, signals with carrier frequency in the radiofrequency range, signals with carrier frequency 500 kHz, signals with one component in the radiofrequency range, signals with one component in the range 250-1000 kHz. The connector 240 can be configured to carry temperature measurement signal(s) from the electrode to an RF generator or another temperature measurement device, as if familiar to one skilled in the art. In the embodiment presented in FIG. 2, the generator plug 240 comprises two pins 242 and 243, of which one can both connect to one output pole of an RF generator and to one pole of the RF generator's temperature sensing circuit, and of which the other can connect to the second pole of the RF generator's temperature sensing circuit. For example, pin 242 can connect to one lead from a thermocouple or thermistor sensor in the active tip 200 of the electrode, and pin 243 can connect to the other lead from the said thermocouple or thermistor sensor in the active tip 200 of the electrode. The connector 240 can be configured to carry other signals, such as additional temperature measurement signals, as is familiar to one skilled in the art. In one embodiment, the connector 240 can have more than two pins. In one embodiment, the connector 240 can have three pins. In one embodiment, the connector 240 can have at least three pins, of which one carries therapeutic and/or diagnostic signals from a generator to the electrode, and the other two connect to a thermocouple contained in the electrode.

The injection port 250 can be configured to carry injected fluids into and through the cables 230, the hub 220, the shaft 210, and out the tip 200. The injection port 250 can be configured to aspirate fluids from the electrode tip 200, for example to confirm proper placement of the electrode tip 200, as is familiar one skilled in the art of epidural anesthesia. The injection port can be a female luer injection port. The port 250 can have a luer lock. The port 250 can have a cap. The cable 232 connecting the luer injection port can have an external clamp to prevent outflow of fluids.

Figure 2A:
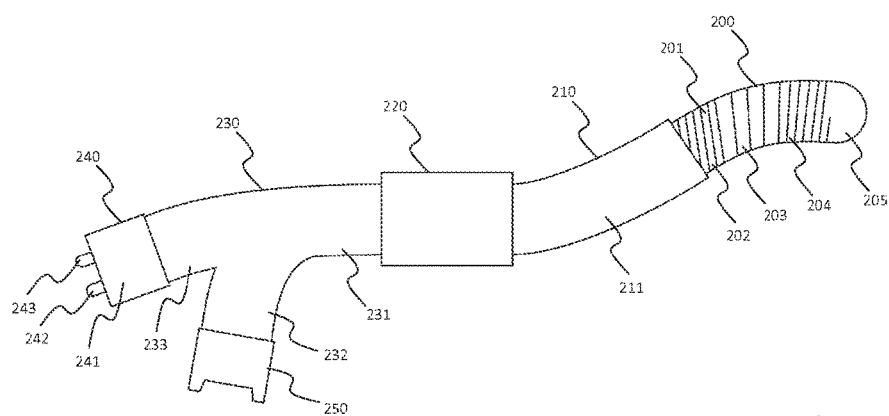
FIG. 2A is a schematic diagram showing in an external view a unitized injection electrode with a flexible active tip, a flexible shaft, an injection port, and a generator connector.

FIG. 2A presents one embodiment of the present invention in which the shaft 210 and tip 200 are positioned in one example of a flexed position.

Figure 2B:
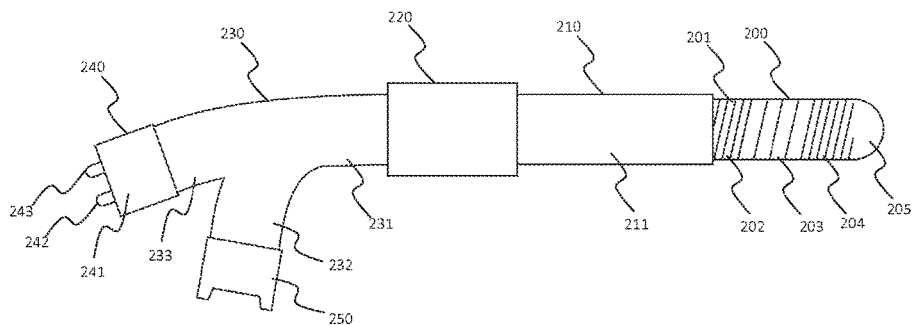
FIG. 2B is a schematic diagram showing in an external view a unitized injection electrode with a flexible active tip, a flexible shaft depicted in a straight position, an injection port, and a generator connector.

FIG. 2B presents the electrode shown in FIG. 2A, where its flexible tip 200 and flexible shaft 210 are in substantially straight position.

Figure 2C:
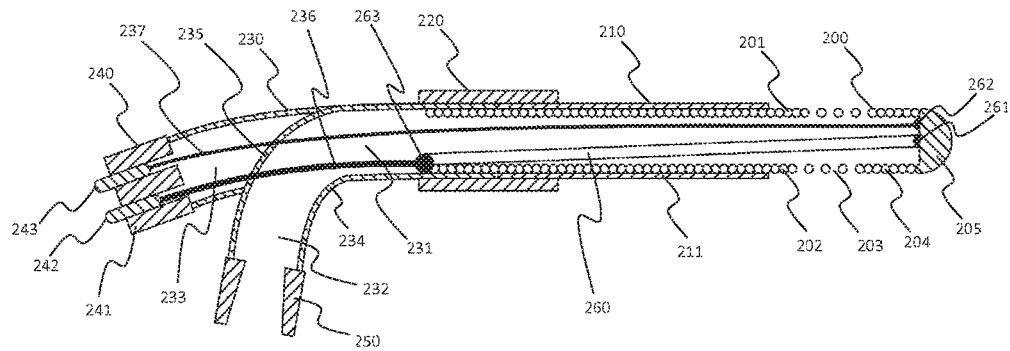
FIG. 2C is a schematic diagram showing in a section view a unitized injection electrode where a coil is used in the construction of the shaft and active tip, and where the electrode has a an integrated stylet, temperature sensor, injection port, and a generator connector.
Figure 2D:
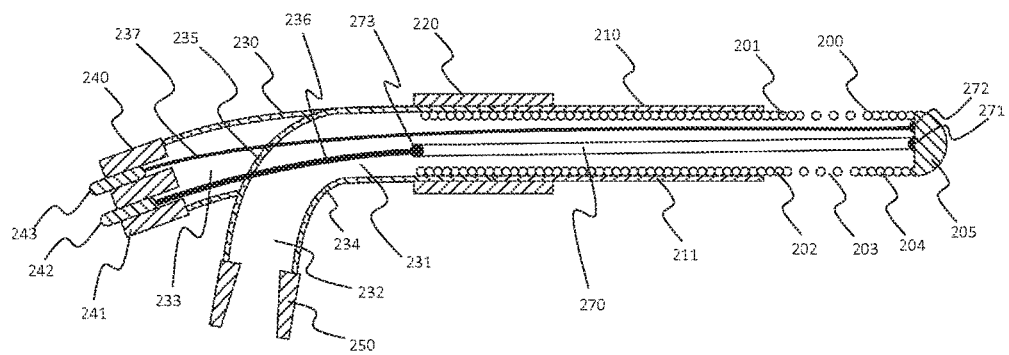
FIG. 2D is a schematic diagram showing in a section view a unitized injection electrode where a coil is used in the construction of the shaft and active tip, and where the electrode has a an integrated stylet, temperature sensor, injection port, and a generator connector.
Figure 2E:
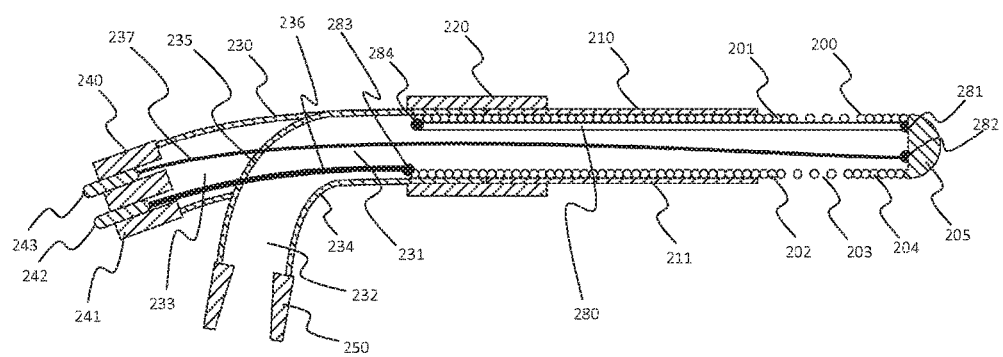
FIG. 2E is a schematic diagram showing in a sectional view a unitized injection electrode where a coil is used in the construction of the shaft and active tip, and where the electrode has a an integrated safety strap, temperature sensor, injection port, and a generator connector.

FIG. 2C, FIG. 2D, and FIG. 2E presents three embodiments of the internal construction of the electrode from FIGS. 2A and 2B, shown in cross-sectional views. Referring now to FIG. 2C, FIG. 2D, and FIG. 2E, the coil 201 is shown in a cross-sectional view wherein round-wire winds appear substantially elliptical. In another embodiment of coil 201, the cross-section of the coil 201 does not appear as an ellipse, for example if flat wire is used to construct the coil 201, the cross section has a substantially rectangular. In one example, the coil 201 is a stainless steel spring coil, which is familiar to one skilled in the art of epidural catheters. The closed distal end 205 of the tip 200 is shown in cross-section. The insulation 211 is shown in a cross-sectional view wherein its tubular structure appears on both sides of the coil 201. In one example, the insulation 211 is a flexible plastic tube, familiar to one skilled in the art of epidural catheters. In one example, the insulation 211 is constructed from a flexible plastic tube within which is another coating, as is familiar to one skilled in the art of epidural catheters. The hub 220 is shown in cross-section wherein its tubular structure appears on both sides of the insulation 211 and the tubing 234. In one example, the hub 220 is a rigid structure composed of a plastic tube and glue that prevents fluid leakage out from the coil 201, insulation 211, and injection tube 234.

The injection tube 234 is shown in a cross-sectional view wherein its tubular structure appears on opposite sides of the central lumen of the injection branch 232 and the root 231 of the cable 230. The injection tube 234 connects the injection port 250 and the hub 220. The injection tube 234 provides a channel through which fluids injected into the injection port 250 can flow into the shaft 210, into the tip 200, and then out from spaces between the coil loops of the tip 200, preferentially through the larger gaps between coil loops in the outflow section 203 of the tip 200. The injection port 250 is shown in a cross-sectional view wherein it appears on opposite sides of the opening at the end of the injection port branch 232 of the cable 230. The port 250 can be a female luer connector. The connector branch 233 of the cable 230 is shown in cross-sectional view so that its walls appear on opposite sides of the internal space through which wires 236 and 237 travel from the generator connector 240 into the root 231 of the cable 230. The connector 240 is shown in a cross-sectional view wherein pins 242 and 243 and mounted within the body 241, which appears in three parts around and between the pins 242 and 243. It is understood that the wires 236 and 237 can each be constructed from multiple pieces of wire, rod, tubing, solder joints, crimps, hooks, and other elements familiar to one skilled in the art of medial device manufacturing.

The wall 235 of the injection tube 234 limits fluid flow into the connector branch 233 of the cable 230. It is understood that this wall portion 235 can, in another embodiment, be constructed of a different material from that of the tube 234; for example, from a glue plug. The wires 236 and 237 travel through the wall 235. It is understood that other embodiments of the construction of the cables 230 can be used to provide both connection to a generator and a pathway for injection or fluids. For example, the cable constructions presented in U.S. Pat. No. 7,862,563 by E R Cosman Sr and E R Cosman Jr can be used. For example, the cable 230 can be constructed like the cable of the Cosman CU electrode, sold by Cosman Medical, Inc.

The wire 236 can be configured to carry electrical signal output from an RF generator and/or a stimulation waveform generator. The wire 236 can be composed of a conductive material, such as copper. The wire 236 can be coated with an electrical insulator. The wire 236 can be bare. The wire 236 can be configured to connect via pin 242 to both the electrical signal output of a generator, such as an RF generator, and to the first terminal of a temperature-monitoring circuit, which can be integrated into the same generator or which can be housed in a separate unit. The wire 237 can be configured to connect via pin 243 to the second terminal of the said temperature monitoring circuit. The wire 237 can be an electrically-insulated constantan wire. In another embodiment pin 242 connects to the electrical signal output of a generator, wire 236 carries signals from the output of said generator, pin 243 has isolated prongs each of which connects to a isolated terminal of a temperature-monitoring circuit, and wire 237 is an bifilar thermocouple wire, such as a copper-constantan bifilar.

Referring now specifically to FIG. 2C, the unitized injection electrode includes a central wire 260 within the inner lumen of the coil 201. The central wire 260 can be configured to stiffen the shaft 210 and the tip 200 of the electrode. The central wire 260 can be configured to provide sufficient stiffness for epidural placement of the electrode, and limited stiffness to prevent puncture of sensitive structures around the epidural space, as is familiar to one skilled in the art of epidural catheters. The central wire 260 can be a stainless steel rod. The central wire 260 can be copper. The central wire 260 can be a tapered metal rod. The central wire 260 can be a rod with a substantially circular cross section. The central wire 260 can be a hollow tube. The central wire 260 can be a plastic rod. The central wire 260 can be a rod with a substantially rectangular cross section. The central wire 260 can be electrically conductive. The central wire 260 can be electrically insulative. The rod 260 can be a bare metal structure. The rod 260 can be covered by an electrically-insulative coating. The central wire 260 can have an outer dimension in the range 0.001" to 0.016". The central wire 260 can have an outer diameter 0.010". The central wire can have an outer diameter 0.11". The central wire 260 can have an outer diameter 0.012". The central wire can have an outer diameter 0.013". The central wire 260 can have an outer diameter 0.014". The central wire can have an outer diameter greater than 0.016". The central wire 260 can have an outer diameter configured to fit within the coil 201 and to allow injected fluid to flow from one end of the coil to the other. The central wire 260 can be configured to conduct electrical signals, such as high frequency signals, RF output, and nerve stimulation signals, from a generator to the tip 200 of the electrode. The central wire 260 can be configured to reduce the impedance of electrical potentials, such as high frequency electrical waveforms, radiofrequency potentials, and nerve stimulation waveforms, between the generator connector 240 and the uninsulated metallic electrode tip 200. The dimensions of the central wire 260 can be configured to provide a flow path of desired area for injected fluids along the electrode shaft.

The central wire 260 can be attached at the distal end of the coil 201 and at the proximal end of the coil 201; one advantage of this embodiment of the invention is that the central wire 260 prevents extension of the coil 201 if its distal end 204 or the closed end 205 is caught in some anatomy, such as between two vertebra. The central wire 260 can carry electrical signals from the generator to the tip 200 of the coil 201; one advantage of this of this embodiment of the invention is that it reduces the electrical impedance between the generator and the active tip 200 of the electrode. The central wire 260 can be configured to maintain a bent configuration. The central wire 260 can be configured to maintain a bent configuration when bent by the user, such as a physician. An advantage of central wire 260 holding a bend is that a bend can be imposed in the electrode shaft. An advantage of a bent electrode shaft is that the bend can maneuvering of the electrode in the human body, such as in the epidural space.

The central wire 260 is connected at junction 263 to both the proximal end of the coil 201 and to the wire 236. The junction 263 can be electrically conductive. The junction 263 can create an electrically connection between the wire 263 and the coil 201. The junction 263 can create an electrical connection between the wire 263 and the central rod 260. The junction 263 can be configured to transmit electrical signals from the wire 263 to the coil 201, either by direct electrical connection or the wire 263 to the coil 201, by electrical connection between the wire 263 and rod 260 and then electrical connection between the rod 260 and the coil 201 at junction 261, or both. In one example, the junction 263 is a solder joint. In another example, the junction 263 includes both a weld and a solder joint. In another example, the junction 263 includes glue. In another example, the junction 263 includes a mechanical lock. In another example the junction 263 is a weld, such as a laser weld. In one example, the junction 263 is a solder joint that incorporates the coil 201, the wire 236, and the central wire 260. In another example, the junction 263 is a solder joint between the wire 236 and the central wire 260, and the central wire 260 is configured so that it mechanically locks with the coil 201; for instance, the central wire 260 can be folded over on itself so that it hooks around the proximal end of the coil 201. In another example, the junction can be a laser weld between the central wire 260 and the coil 201, and a solder joint between the wire 236 and the coil 201. It is understood that the junction 263 can take other forms as is familiar to one skilled in the art of medical device manufacturing. In another embodiment the central wire 260 can be anchored to another element of the hub 220.

The central wire 260 is connected to the closed distal end 205 of the tip 200 at junction 261. The junction 261 can be electrically conductive. the junction 261 can be electrically insulative. The junction 261 can be configured so that the rod 260 and the closed distal end 205 connected electrically. In one example, the junction 261 is part of the weld that formed the closed distal end 205. It is understood that the junction 263 can take other forms as is familiar to one skilled in the art of medical device manufacturing, including without limitation, gluing, welding, soldering, crimping, hooking, mechanical locking.

The wire 237 is connected to the closed distal end 205 of the tip 200 at junction 262. The junction 262 can be electrically conductive. The junction 262 can be electrically insulative. The junction 262 can be configured so that the rod 260 and the closed distal end 205 connected electrically. In one example, the junction 262 is part of the weld that formed the closed distal end 205. It is understood that the junction 263 can take other forms as is familiar to one skilled in the art of medical device manufacturing, including without limitation, gluing, welding, soldering, crimping, hooking, mechanical locking. In one embodiment the wire 237 is an insulated constantan wire, the coil 201 is stainless steel, and the junction 262 is electrically conductive such that it forms a thermocouple junction. In one embodiment the wire 237 is an insulated metal wire, the coil 201 is composed of a dissimilar metal, and the junction 262 is electrically conductive such that it forms a thermocouple junction. In one embodiment, the closed distal end 205 is a weld that incorporates both the wire 237 and the coil 201. In one embodiment, the closed distal end 205 is a solder joint that incorporates both the wire 237 and the coil 201. In one embodiment, the wire 237 is a thermocouple bifilar, such as a copper-constantan bifilar, as is familiar to one skilled in the art of thermocouples, and the junction includes an element that forms the thermocouple junction between the two wires of the bifilar 237, for example by means of a weld, and an element that mechanically attaches the distal end of the bifilar wire 237 to the closed end of the coil 205.

It is understood in different embodiments that the wire 237 can take any one of a number of paths along the shaft 210, for example, entirely within the coil inner lumen, between the coil 201 and insulation 210, or passing into the inner lumen and out into the space between the insulation 211 and the coil 201 by passing between adjacent loops of the coil 201 any number of times.

In one example, the closed end of the coil is a weld that connects the wire 237, the rod 260, and the coil 201. In one example, the closed end of the coil is a solder joint that connects the wire 237, the rod 260, and the coil 201.

In one example, the wire 236, the central wire 260 and the coil 201 itself carry electrical output of an electrosurgical generator, such as radiofrequency and/or stimulation waveforms, to the tip 200 of the electrode. In one example, wires 236 and 237 connect to opposite poles of a temperature sensor, such as a thermocouple junction, at the tip 200 of the electrode, and conduct signals from said temperature sensor to a temperature monitoring system.

In another embodiment, the temperature connection 243, the wire 237, and the junction 262 can be omitted. In this embodiment, electrical signals are conducted through the electrode without temperature monitoring. An advantage of this embodiment is that it is easier to build. An advantage of this embodiment is that the electrode provides for stimulation-guided placement in the epidural space. An advantage of this embodiment is that it can be used for non-temperature-monitored application of RF therapy, such as thermal RF lesioning and pulsed RF treatment.

In one embodiment of the present invention, an example of which is shown in FIG. 2C, the unitized electrode is configured for placement in the epidural space, temperature monitoring of the electrode's active, tip, and delivery of radiofrequency signals via the electrode's active tip; wherein the electrode consists of a metallic coil with a proximal and distal end, an electrically insulative sheath that covers the proximal length of the coil and leaves the distal end of the coil exposed, a temperature sensor in exposed distal end of the coil, a port that allows for injection of fluids into the inner lumen of the coil, and a connector to an electrosurgical generator. In a more specific embodiment, the unitized electrode includes a central wire that mechanically connects the distal end of the coil to proximal hub structures. In a more specific embodiment, the said spring coil is stainless steel. In a more specific embodiment, a thermocouple junction is formed at the distal tip of the electrode by welding a constantan wire to the coil and to the central metallic wire.

Referring now to FIG. 2D, the unitized injection electrode includes a central wire 270. In this embodiment, junction 273 connects the central wire 270 and the wire 236, and junction 271 connects the central wire 270 to the closed distal end 205 of the active tip 200. Junction 272 is the connection of the wire 237 to the closed distal end 205 of the active tip 200. In one embodiment, high frequency electrical signals are carried to the active tip 200 of the electrode via wire 236 and rod 270. In one embodiment, the junction between wires 237 and 270 at the closed distal end 205 form a thermocouple junction. In one embodiment, the wire 236 is a bifilar wire that carries signals from a temperature sensor at junction 272. The junction 273 and wire 236 can be configured to anchor the rod 270 to the generator connector; an advantage of this configuration is that the wire 270 prevents the tip 200 from separating from the electrode. The junction 273 can include elements familiar to one skilled in the art of medical device construction, including soldering, welding, crimping, clamping, gluing, hooking, and twisting. In one example, the rod 270 is cover by electrically insulation along its length, so that signals carried by wire 236 are not conveyed to the closed distal end 205 by the coil 201. In another example, the rod 270 is uninsulated so that electrical signals are carried to the active tip 200 via the coil 201 if the coil touches the central wire 270. The central wire 270 can be a metal rod. The central wire 270 can be a flat wire with rectangular cross section. The central wire 270 can have outer diameter at a value in the range 0.001 to 0.018 inches. The central wire 270 can have outer diameter 0.011 inches. The central wire 270 can have a rectangular cross section with cross section substantially similar to 0.003 inches by 0.009 inches. The central wire 270 can be dimension and geometry configured to provide desired separation force between the tip 200 and the hub 220. The central wire 270 can be dimension and geometry configured to provide desired separation force between the distal end of the coil 201 and the proximal end of the coil 201. The central wire 270 can be configured to produce a desired flexibility for the shaft 210 and tip 200. The central wire 270 can be configured to maintain a bent configuration. The central wire 270 can be configured to maintain a bent configuration when bent by the user, such as a physician. An advantage of central wire 270 holding a bend is that a bend can be imposed in the electrode shaft. An advantage of a bent electrode shaft is that the bend can maneuvering of the electrode in the human body, such as in the epidural space. The central wire 270 can be configured so that the electrode is suitable for placement in the epidural space.

Referring now to FIG. 2E, the unitized injection electrode includes a safety strap 280. The safety strap 280 is connected to the distal end of the coil 201 at junction 281 and to the proximal end of the coil 201 at junction 283. The wire 236 is connected to the coil 201 at junction 283. The wire 237 is connected to the distal end of the coil 201 at junction 282. The wire 236 and the coil 201 itself can carry RF output and/or stimulation out to the active tip 200 of the electrode from a medical electrosurgical generator to which connector 240 is attached. In one embodiment, the junction between the spring coil 201 and the wire 237 at the closed distal end 205 of the coil 201 forms a temperature sensor, such as a thermocouple, and the wires 236 and 237 carry signals from said temperature sensor to the connector 240. In another embodiment, the wire 237 is a bifilar wire, such as a copper-constantan thermocouple wire, and junction 272 is a temperature-sensing junction, such as a thermocouple weld, that is mechanically anchored to the tip 200. The safety strap 280 can be a metal rod. The safety strap 280 can be a flat wire with rectangular cross section. The safety strap 280 can have outer diameter at a value in the range 0.001 to 0.018 inches. The safety strap 280 can have outer diameter 0.010 inches. The safety strap 280 can have a rectangular cross section with cross section substantially similar to 0.003 inches by 0.009 inches. The safety strap 280 can be dimension and geometry configured to provide desired separation force between the tip 200 and the hub 220. The safety strap 280 can be dimension and geometry configured to provide desired separation force between the distal end of the coil 201 and the proximal end of the coil 201. The safety strap 280 can be configured to produce a desired flexibility for the shaft 210 and tip 200. The safety strap 280 can be configured to maintain a bent configuration. The safety strap 280 can be configured to maintain a bent configuration when bent by the user, such as a physician. An advantage of a safety strap 280 holding a bend is that a bend can be imposed in the electrode shaft. An advantage of a bent electrode shaft is that the bend can maneuvering of the electrode in the human body, such as in the epidural space. The safety strap 280 can be configured so that the electrode is suitable for placement in the epidural space.

Figure 3:
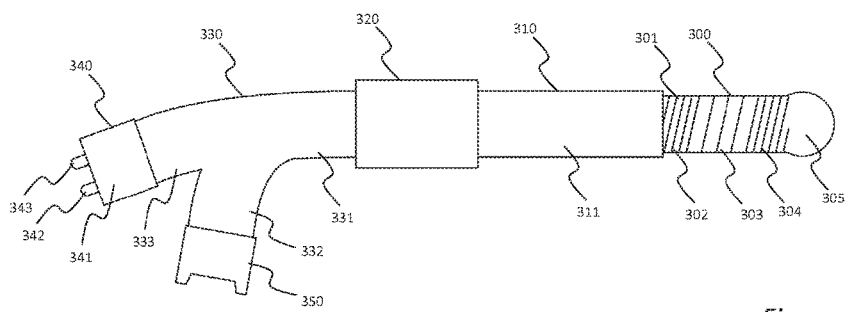
FIG. 3 is a schematic diagram showing a unitized injection electrode with a flexible active tip, closed distal end with diameter larger than the outer diameter of the proximal part of the active tip, a flexible shaft, an injection port, and a generator connector in an external view.

FIG. 3 presents a unitized injection electrode for which the closed distal end 305 has a larger outer diameter than the outer diameter of the rest of the active tip 300, in accordance with one aspect of the present invention. In one embodiment, the electrode in FIG. 3 is analogous to the electrode presented in FIG. 2. The electrode comprises a flexible active tip 300, an electrically-insulated flexible shaft 310, a hub 320, cables 330, electrical signal connector 340, and injection port 350. The electrode can be constructed so that its active tip 300, insulated shaft 310, hub 320, cables 330, signal connector 340, and injection port 350 are inseparably connected. The distal end of the electrode is the end of the active tip 300, and the proximal end of the electrode is end of the cables 230. As in the electrode presented in FIG. 2A, in one embodiment, the tip 300 and shaft 310 include a coil 201, and electrical insulation 311 covers the coil in the shaft region 310 and is absent in the tip region 300, to form the metallic active tip 300 of the electrode. The tip includes an outflow region 303 that can be configured to preferentially emit fluids injected into the port 350. The active tip 300 can be configured to be energized by a generator attached to connector 340. Temperature can be measured at the active tip 300 by a temperature measurement circuit attached to the connector 340. The length of the electrode's shaft 310 can be configured for epidural placement. The length of the electrode's active metallic tip 300 can be in the range 2-30 mm or more, and it can be configured by performing RF and pulsed RF therapy.

FIGS. 4A and 4B each present a unitized injection electrode with movable stylet 460, in accordance with one aspect of the present invention. The electrode with stylet 460 can be configured for placement in the epidural space. Referring to both FIG. 4A and FIG. 4B, the stylet 460 comprises a hub 461 and shaft 462. The electrode, within which the stylet 460 can move, comprises an active tip 400, an electrically insulated shaft 410, a hub 420, cables 430, electrical signal connector 440, and injection port 450. The electrode can be constructed so that its active tip 400, insulated s haft 410, hub 420, cables 430, signal connector 440, and injection port 450 are inseparably connected. In FIGS. 4A and 4B, the stylet 460 is shown positioned within the unitized injection electrode. The tip 400 can be constructed from a metallic coil 401, such as stainless steel spring coil, and have regions of tight coiling 402 and 404, and regions of looser coiling 403 to allow for preferential outflow of fluids injection into port 450, and a closed distal end 405 that is, in one embodiment, blunt and atraumatic. The coil 401 can extend into the shaft region 410, where it is covered by electrical insulation 411. The active tip 400 can be configured to be energized by a generator attached to connector 440. Temperature an be measured at the active tip 400 by a temperature measurement circuit attached to the connector 440. The stylet hub 461 can be configured to be grasped by human fingers. The stylet hub 461 can be omitted. The electrode hub 420 can be omitted. The length of the electrode's shaft 410 can be configured for epidural placement. The length of the electrode's shaft 410 can be in the range 12 to 33 inches. The length of the electrode's active metallic tip 400 can be in the range 2-30 mm or more, and it can be configured by performing RF and pulsed RF therapy. The diameter of the electrode shaft 410 and tip 400 can be in the range 21 gauge to 18 gauge. Electrode shaft 410 and tip 400 can be substantially equal to 19 gauge. Electrode shaft 410 and tip 400 can be substantially equal to 20 gauge. Electrode shaft 410 and tip 400 can be configured for epidural placement.

The distal end of the electrode is the end of the active tip 400, and the proximal end of the electrode is end of the cables 430. Electrode structures that are more distal are closer to the distal tip 405. Electrode structures that are more proximal are closer to the generator connector 440 and/or to the injection port 450. The distal end of the stylet 460 is the distal tip 463. the proximal end of the stylet 460 is the handle 461.

When inserted, the stylet 460 can enter the port 450, travel through branch 432 and 431 of the cables 430, the hub 420, shaft 410, and all, part, or none of the tip 400. In one embodiment, not shown, the cable branches 431 and 432 can present a straight path through which the stylet moves. In one embodiment, the cable branches 431 and 432 can be rigid in whole or in part to facilitate movement of the stylet shaft 462 within them. In one embodiment the cable branch 433 that is associated with the generator connector 440 is flexible. In another embodiment the cable branch 433 that is associated with the generator connector 440 is rigid.

The shaft 410 and tip 400 can both be flexible when the stylet 460 is inserted and when the stylet 460 is not inserted. The stylet can be physically separable 460 from the electrode. An advantage of the embodiment where the stylet 460 can be fully withdrawn and removed from the electrode is that when the stylet is fully removed from the electrode, fluids can be injected into port 430 and delivered to anatomy nearby the electrode tip 400. The stylet 460 can be physically inseparable from the electrode, for example, by providing a mechanical element that prevents removal of the stylet from the electrode. The electrode and stylet 460 can be configured to enable the user to move the stylet 460 within the inner lumen of the electrode; an advantage of a unitized injection electrode with a moveable stylet 460, is that the stylet 400 can be moved to adjust the flexibility of the electrode tip 400 and shaft 410. The electrode and stylet 460 can be configured for placement in the epidural space of the human body. The electrode can be configured to provide for radiofrequency treatment and injection of fluids, such as radiocontrast agents, anesthetics, neurolytics agents, alcohol phenol, saline, hyaluronidase, local anesthetic, corticosteroids, hypertonic saline. The electrode can be configured to monitor the temperature at the tip 400 of the electrode. The electrode and stylet 460 can be configured for stimulation-guided epidural anesthesia, such as lysis of adhesions. The electrode can be configured to be radiopaque. The stylet shaft 462 can be configured to be radiopaque. An advantage of the electrode being radiovisible is that x-ray guidance, such as fluoroscopy, can be used to position the electrode in the human body. An advantage of the stylet 460 being radiovisible is that x-ray guidance, such as fluoroscopy, can be used to position the electrode in the human body. The construction of the stylet 460 can be that of epidural catheters. The stylet shaft 462 can be a stainless steel rode. The stylet shaft 462 can have outer diameter that is a value in the range 0.001 inches to 0.018 inches. The stylet shaft 462 can have outer diameter greater than 0.018 inches. The stylet shaft 462 can have outer diameter that is 0.010 inches. The stylet shaft 462 can be configured to be flexible enough to move through the cables 430, shaft 410, and tip 400. The stylet shaft 462 can be configured to maintain a bent configuration. An advantage of the stylet 460 holding a bend is that bend can be imposed in the electrode shaft when the stylet 460 is in place. An advantage of a bent electrode shaft is that the bend can maneuvering of the electrode in the human body, such as in the epidural space.

Referring now to FIG. 4A, an external view of a unitized injection electrode and stylet 460 is shown.

Referring now to FIG. 4B, a cross-section of the unitized injection electrode is presented and shows one embodiment of its construction. The shaft 462 of the stylet 460 is within the inner lumen of the coil 401, which appears as a series of substantially circular elements in the cross-sectional view. The tip of the stylet 463 can touch the inner surface of the electrode's distal end 405 when the stylet is fully inserted. The tip of the stylet 463 can be configured so that is cannot touch the inner surface of the electrode's distal end 405 when the stylet is fully inserted. One advantage of the distal tip of the stylet's 463 not being able to touch the inner surface of the electrode's distal end when fully inserted is that it ensures the distal end of the coil 401, for instance the region 404, is less stiff than the rest of the tip 400 and shaft 410 at all times.

Pin 442 of connector 440 can be configured to connect to the electrical output of a medical electrical generator, such as an RF generator or a nerve stimulator. Pin 442 is connected to wire 436. Wire 436 is connector to the coil 401 and the safety strap 480 at junction 484. Safety strap 480 is connected to the coil 401 at its distal end 405 at junction 481. Pin 442, wire 236, coil 401, strap 480 can be configured to carry electrical signals, such as RF generator output, to the active tip 400 of the electrode from a medical generator connected to pin 442. In another example, the safety strap 480 can be electrically insulative. The wire 436 can include a conductive metal, such as copper. The safety strap 480 can include a conductive metal, such as stainless steel. The safety strap 480 can be a stainless steel flat wire. The cross-section of the safety strap can be substantially rectangular with dimension substantially similar to 0.005 inches by 0.010 inches. One advantage of the safety strap 480 being a flat wire is that the safety strap 480 has a low profile. One advantage of the safety strap 480 being a flat wire is that the safety strap 480 obstructs less of the fluid flow path within the lumen of the coil 401. One advantage of the safety strap 480 being a flat wire is that a larger diameter stylet shaft 462 can passed into the inner lumen of the coil 401. The safety strap 480 can be configured to help prevent the coil 401 from changing length and/or uncoiling with the body. In another embodiment, the safety strap 480 can be omitted, in which case junction 484 is between wire 436 and coil 401, and the coil 401 itself carries electrical signals to its active tip 400.

In one embodiment pin 443 connects to one pole of temperature-monitoring circuit and pin 442 connects to the other pole of said temperature-monitoring circuit. In this embodiment, wire 437 connects to pin 443 and is electrically-insulated constantan wire, and the safety strap 480 and coil 401 can both be stainless steel. The distal end of the coil 405 can be a weld that connects the coil 401, the strap 480, and the constantan wire 347 to form a thermocouple junction from which the said temperature-monitoring circuit measures temperatures. In another embodiment, pin 443 has two electrically-isolated prongs that connect to both poles of a temperature-monitoring circuit, the wire 437 is a bifilar of dissimilar metals, such as copper-constantan thermocouple wire, the junction 482 is the thermocouple formed by connection of the two wires of the bifilar 437 to form a thermocouple, and the temperature-monitoring circuit measures temperature form the thermocouple 482; the thermocouple 482 can be connected to the coil 401 within the length of the tip or to its closed distal end 405.

It is understood, that the wire 437 can be positioned outside the coil for all or part of the length of the hub 420 and shaft 411. It is understood, that the wire 437 can pass into and out of the coil 401 along its length by passing between adjacent loops of the coil 401. One advantage of the wire 437 being outside the inner lumen of the coil 401 is that it is like likely to be damaged by the movable stylet shaft 462.

Figure 5A:
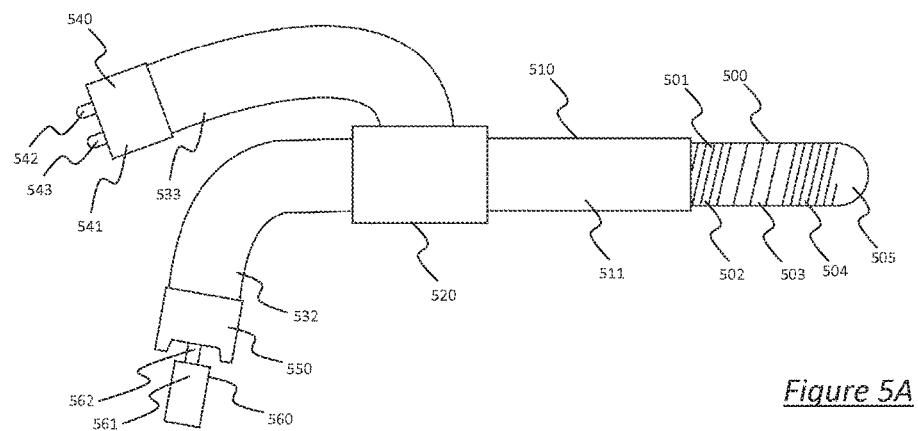
FIG. 5A is a schematic diagram showing connector in an external view a unitized injection electrode system with a flexible active tip, a flexible shaft depicted in a straight position, an injection port, a generator connector, and a moveable stylet, where the injection port and generator connector are each connected separately by means of a dedicated tube to the proximal end of the electrode.
Figure 5B:
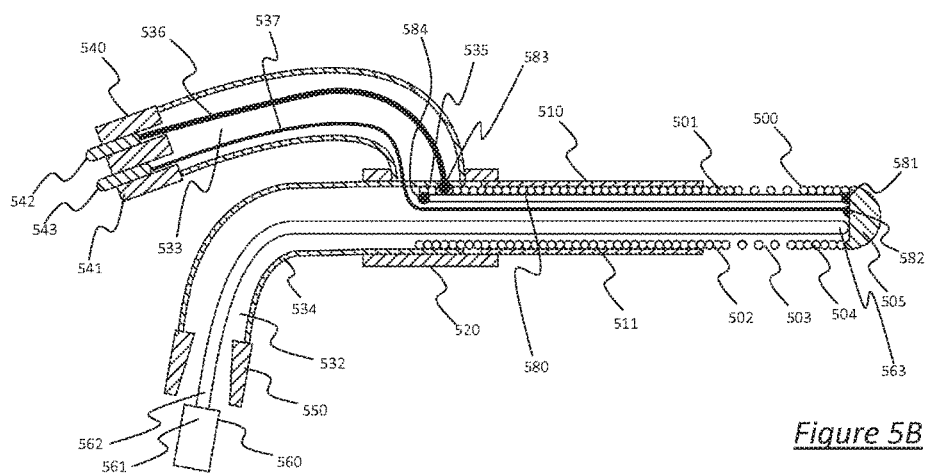
FIG. 5B is a schematic diagram showing in a sectional view a moveable stylet positioned inside a unitized injection electrode where a coil is used in the construction of the shaft and active tip, where the electrode has a temperature sensor, injection port, and a generator connector, and where the injection port and generator connector are each connected separately by means of a dedicated tube to the proximal end of the electrode.

FIG. 5 presents a unitized injection electrode with moveable stylet in accordance one aspect with the present invention. FIG. 5A shows an external view of the unitized injection electrode. FIG. 5B shows on embodiment of the internal construction of the unitized injection electrode in a cross-section view. In one embodiment, the embodiments presented in FIG. 5A and FIG. 5B are analogous to the embodiments presented in FIG. 4A and FIG. 4B, with the difference that in FIG. 5, the injection cable branch, labeled 532 in FIG. 5 and labeled 432 in FIG. 4, and the generator cable branch, labeled 533 in FIG. 5 and labeled 433 in FIG. 4, are connected directly to the hub, labeled 520 in FIG. 5 labeled 420 in FIG. 4, whereas in FIG. 4 the injection cable branch and generator cable branch connect to a root cable branch 431 that connects to the hub 420. In one embodiment, the injection electrode with moveable stylet is configured for RF therapy. In one embodiment, the injection electrode with moveable stylet is configured to be placed in the epidural space. In one embodiment, the injection electrode with moveable stylet 560 is configured for injection of fluid through the tip 500. In one embodiment, the stylet 560 can be removed from the electrode to allow for delivery of fluids from the tip 500 by means of injection into port 550. In one example, the electrode shaft 510 and tip 500 are flexible. In one embodiment, the injection electrode is configured to measure the temperature of tissue in contact with the active tip 500 of the electrode. In one embodiment, the injection electrode is configured to effect temperature-controlled radiofrequency treatment, including pulsed radiofrequency therapy, of nerves by means of placement of the electrode in the epidural space of a human patient in order to manage said patient's pain. In one embodiment, the unitized injection electrode with moveable stylet is configured to apply radiofrequency electric fields, including pulsed radiofrequency electric fields, to spinal nerves, spinal nerve roots, dorsal spinal nerve roots, and/or dorsal root ganglia, by placement of the electrode in the epidural space and/or the spinal foramina.

The distal end of the electrode is the end of the active tip 500, and the proximal end of the electrode is end of the cables 530. Electrode structures that are more distal are closer to the distal tip 505. Electrode structures that are more proximal are closer to the generator connector 540 and/or to the injection port 550. The distal end of the stylet 460 is the distal tip 563. The proximal end of the stylet 560 is the handle 561.

The unitized injection electrode has tip 500 comprising a metallic coil 501 with distal end 505, shaft 510 comprising electrical insulation 511 covering the metallic coil 501, hub 520, generator cable 533, connector 540 comprising body 541 and pins 542 and 543, injection cable 532, injection port 550, and movable stylet 560 comprising hub 561 and shaft 562. In one embodiment, elements 50, 510, 520, 533, 540, 532, and 550 are inseparably connected. In one embodiment injection tube 532 is straight. In one embodiment injection tube 532 is curved. In one embodiment injection tube 532 is flexible. In one embodiment injection tube 532 is rigid. In one embodiment generator cable 533 is flexible. In one embodiment generator cable 533 is rigid. In one embodiment, the stylet shaft 562 is a metal rod. In one embodiment, the stylet shaft 562 is a stainless steel rod. In one embodiment, the stylet shaft 562 is a nitinol rod. One advantage of a moveable stylet 560 is that the flexibility of the electrode shaft 510 and tip 500 can be adjusted by movement of the stylet 560.

In another embodiment, the injection tubing 532 can be omitted and the injection port 550 directly connected to the hub 520. In another embodiment, the generator cable 533 can be omitted and the connector 540 directly connected to the hub 520. In another embodiment, the hub 520 can be omitted, and the injection cable 532 and the generator cable 533 directly connected to the electrode shaft 510. In another embodiment, the hub 520 can be omitted, the injection tube 532 omitted, the injection port 550 directed connected to the electrode shaft 510, and the generator cable 533 directly connected to the electrode shaft 510. In another embodiment, the hub 520 can be omitted, the electrode cable 532 omitted, the injection tube 532 directly connected to the electrode shaft 510, and the generator connector 540 directly connected to the electrode shaft 510. In another embodiment, the hub 520 can be omitted, the electrode cable 532 omitted, the injection tube 532 omitted, the injection port 550 directly connected to the electrode shaft 510, and the generator connector 540 directly connected to the electrode shaft 510. In another embodiment, the injection tube 532 and the injection port 550 can be omitted, the stylet 560 can be inserted directly into the inner lumen of the coil 501, and a separate injection port, such as a tuohy-borst adaptor, can be connected to the shaft when the stylet 560 is withdrawn from electrode to provide for injection of fluid through the electrode into tissue in which the electrode tip is placed.

Referring now to FIG. 5A specifically, an external view of the electrode is shown with the stylet 560 in place within the electrode.

Referring now to FIG. 5B specifically, a cross-sectional view of one embodiment of the internal construction of the electrode is shown with the stylet 560 in place within the inner lumen of the electrode. In one embodiment, the stylet shaft 562 is configured so that when it fully inserted into the electrode, the distal tip 563 of the stylet 562 contacts the inner surface of the distal tip 505 of the electrode. In another embodiment, the stylet shaft 562 is configured so that when it fully inserted into the electrode, the distal tip 563 of the stylet shaft 562 is does not contact the inner surface of the distal tip 505 of the electrode. Element 535 is configured to limit or prevent the flow of fluid into the generator cable 533. Wire 536 and 537 pass through element 535. In one embodiment, element 535 includes the wall of the injection tube 532. In one embodiment, element 535 includes glue, such as a glue plug. In one embodiment, element 535 includes the wall of the shaft insulation 511. In one embodiment, wire 537 can passes into the inner lumen of the coil 501 via its proximal end, as illustrated in FIG. 5B. In another embodiment, wire 537 can enter the inner lumen of coil 501 by passing between links of the coil 501. Pin 542 is electrically connected to wire 536, which is electrically connected to coil 501 at junction 583, which can be, for example, a weld or solder joint. In one embodiment, electrical output from a generator connected to pin 542 is conducted to the active tip 500 of the electrode via wire 536, junction 583, and coil 501. Pin 543 is electrically connected to wire 537, which is connected to the distal end 505 of the electrode at junction 582. In one embodiment, distal end 505 is a weld that incorporates the wire 537. In one embodiment, distal end 505 is a solder joint that incorporates the wire 537. In one embodiment, distal end 505 is a glue joint that connects to the wire 537. In one embodiment, wire 537 is a constantan wire, the coil 501 is stainless steel, the connection between the coil 501 and the wire 537 is a thermocouple junction, pin 542 is configured to be attached to a temperature-measurement circuit, pin 542 is configured to be attached to the same temperature-measurement circuit, and thereby the temperature of tissue in contact with the distal tip 505 of the electrode. In another embodiment, wire 537 comprises insulated constantan and copper wires whose junction 582 is a thermocouple junction, pin 543 comprises two electrically-isolated pins of which each is connected tone of the two wires comprising wire 537, said two electrically-isolated pins are configured to be connected to a temperature-measurement system, and thereby the temperature of tissue in contact with the electrode tip 500 can be measured. The safety strap 580 can connect to the distal and proximal end of the coil 501 at junctions 581 and 584, respectively. One advantage of the safety strap 580 is that it makes the shaft 510 and tip 500 more robust. In one embodiment, the safety strap 580 can be metallic, such as a stainless steel flat wire. One advantage of a metallic safety strap 580 is that it reduces the electrical impedance between the proximal and distal ends of the coil 501. One advantage of a metallic safety strap 580 is that electrical signals are conducted with less distortion from wire 536 to the active tip 500 of the electrode. In another embodiment, the safety strap 580 can be omitted. In another embodiment, the wire 537 can include elements, such as a wire, that is configured to serve as a safety strap.

Figure 6A:
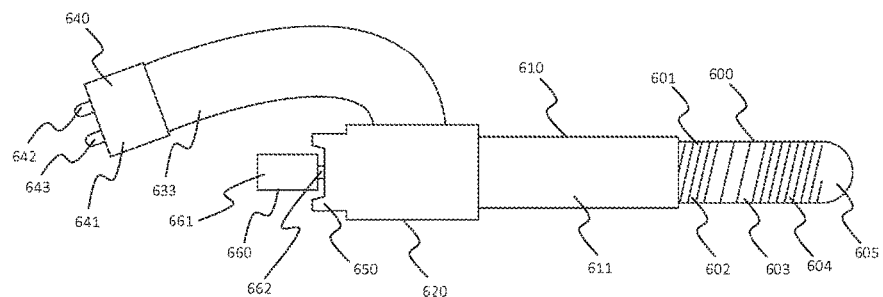
FIG. 6A is a schematic diagram showing connector in an external view a unitized injection electrode system with a flexible active tip, a flexible shaft, an injection port, a generator connector, and a moveable stylet, where the injection port is integrated into the hub at the proximal end of the electrode.
Figure 6B:
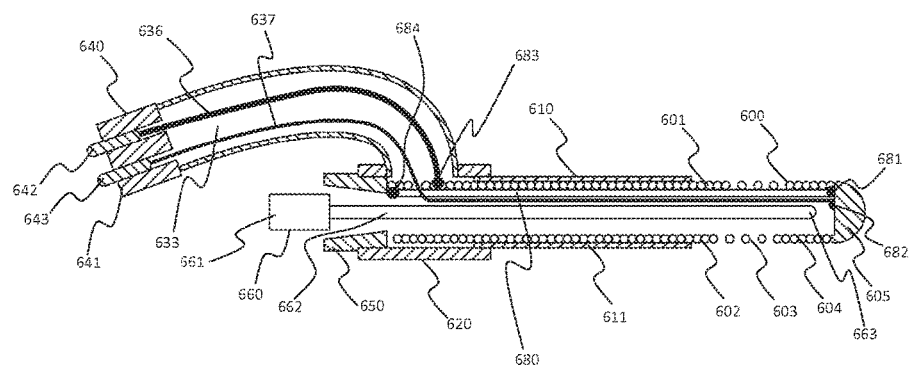
FIG. 6B is a schematic diagram showing in a sectional view a moveable stylet positioned inside a unitized injection electrode where a coil is used in the construction of the shaft and active tip, where the electrode has a temperature sensor, injection port, and a generator connector, and where the injection port is integrated into the hub at the proximal end of the electrode.

FIG. 6 presents a unitized injection electrode with moveable stylet, in accordance with one aspect of the present invention. FIG. 6A shows an external view of the unitized injection electrode. FIG. 6B shows one embodiment of the internal construction of the unitized injection electrode in a cross-section view, with the exterior of the stylet 660 shown. In one embodiment, the embodiments presented in FIG. 6A and FIG. 6B are equivalent to the embodiments presented in FIG. 5A and FIG. 5B, with the difference that the injection cable branch labeled 532 in FIG. 5 is omitted in FIG. 6, and the injection port, labeled 550 in FIG. 5 and labeled 650 in FIG. 6, is directly connected to the hub 620 in FIG. 6. One advantage of the direct connection of the injection port 650 to the hub 620 the pathway for fluid injection can be reduced.

The unitized injection electrode has tip 600 comprising a metallic coil 601 with distal end 605, shaft 610 comprising electrical insulation 611 covering the metallic coil 601, hub 620, generator cable 633, connector 640 comprising body 641 and pins 642 and 643, injection port 650, and movable stylet 660 comprising hub 661 and shaft 662. In one embodiment, elements 600, 610, 620, 633, 640, and 650 are inseparably connected. The tip 600 can have a region 603 for which the coil loops are more loosely spaced than in other regions, such as region 601 and 602.

The distal end of the electrode is the end of the active tip 600, and the proximal end of the electrode is end of the cables 630. Electrode structures that are more distal are closer to the distal tip 605. Electrode structures that are more proximal are closer to the generator connector 640 and/or to the injection port 650. The distal end of the stylet 600 is the distal tip 663. The proximal end of the stylet 660 is the handle 661.

Referring now to FIG. 6B specifically, the electrode has wire 636, wire 637, and safety strap 680. Wire 637 can be a constantan wire that connects to pin 643, and that connects to the distal end 605 of the coil 601 at junction 682 to form a thermocouple junction. Wire 637 can be a thermocouple bifilar terminated by a thermocouple junction 682 that connects to two pins composing pin 643. Pin 643 is configured to provide for monitoring of the tip temperature by connection to a temperature-measurement device. Wire 637 connects to pin 642 and to coil 601 to provide for conduction of electrical signals from a electrosurgical generator attached to pin 642 to the active tip 600 of the electrode. In embodiments where a thermocouple junction is formed between a constantan wire 637 and the distal end 605 or the coil 601, the pin 642 can connect to a temperature-measuring device to provide for monitoring of the temperature of tissue in contact with the active tip 600.

Wire 637 can enter the lumen coil 601 by passing between two loops of coil 601. In another embodiment, the wire 637 can enter the lumen of the coil 601 be passing into the proximal end of the coil 601. In another embodiment, the wire 637 can enter the inner lumen of the coil 601 at a more distal point along the shaft than pictured in FIG. 6B; an advantage of this embodiment is that the stylet shaft 662 and the wire 637 can touch each other over a shorter length. It is understood that a structure can be added to the end of the generator cable 633 where it connects to the hub 620 that is configured to limit flow of fluids into the generator cable 633, such as a glue plug.

Figure 7:
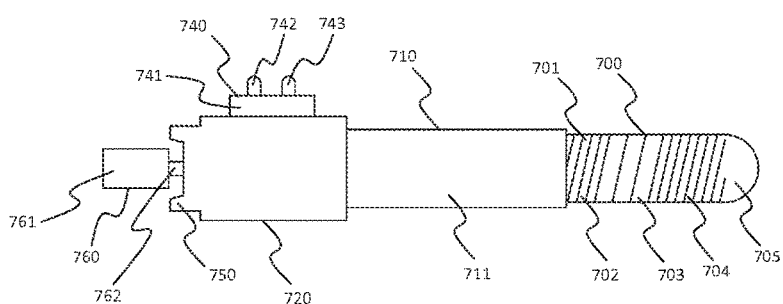
FIG. 7 is a schematic diagram showing connector in an external view a unitized injection electrode system with a flexible active tip, a flexible shaft, an injection port, a generator connector, and a moveable stylet, where the injection port and generator connector are both integrated into the hub at the proximal end of the electrode.

FIG. 7 presents a unitized injection electrode with moveable stylet in an external view. In one embodiment, the embodiments presented in FIG. 7 are equivalent to the embodiments presented in FIG. 6A and FIG. 6B, with the difference that the generator cable branch labeled 633 in FIG. 6 is omitted in FIG. 7, and the injection port labeled 650 in FIG. 6 and labeled 750 in FIG. 7, is directly connected to the hub 720 in FIG. 7. The unitized injection electrode has tip 700 comprising a metallic coil 701 with distal end 705, shaft 710 comprising electrical insulation 711 covering the metallic coil 701, hub 720, connector 740 comprising body 741 and pins 742 and 743, injection port 750, and movable stylet 760 comprising hub 761 and shaft 762. In one embodiment, elements 700, 710, 720, 740, and 750 are inseparably connected. The tip 700 can have a region 703 for which the coil loops are more loosely spaced than in other regions, such as region 701 and 702.

Figure 8A:
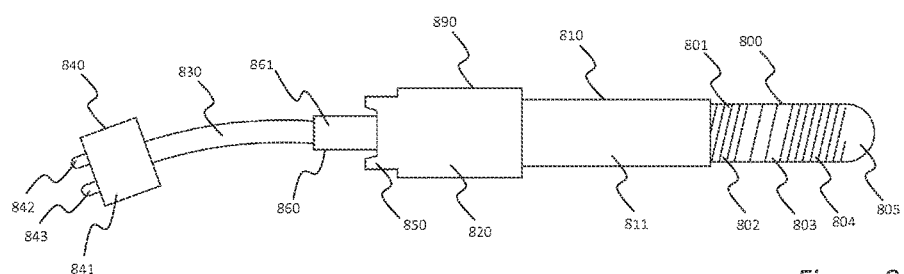
FIG. 8A is a schematic diagram showing in an external view an electrode system comprising a flexible catheter and stylet electrode.
Figure 8B:
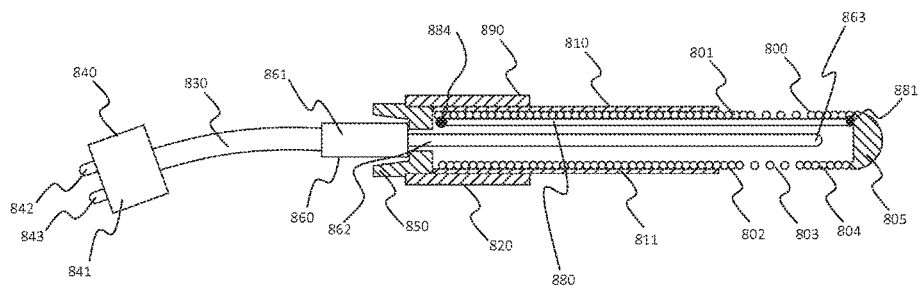
FIG. 8B is a schematic diagram showing in a sectional view an electrode system comprising a flexible catheter and stylet electrode.

FIG. 8 present an injection electrode system comprising a catheter 890 and separate, movable stylet electrode 860, in accordance with one aspect of the present invention. FIG. 8A presents one embodiment of the injection electrode system in an external view. FIG. 8B presents one embodiment of the internal construction of the injection electrode system, wherein the catheter 890 is shown in a cross-sectional view and the electrode 860 is shown from its exterior, positioned within the catheter 890. Referring to both FIG. 8A and FIG. 8B, the catheter 890 comprises a tip comprising coil 801 and distal end 805, shaft 810 comprising insulation 811 outside the coil 801, hub 820, and injection port 850. The electrode 860 comprises shaft 862, hub 860, cable 830, generator connector 840 comprising body 841 and pins 842 and 843. The distal end of the catheter is the end of the distal point 805, and the proximal end of the electrode is end of the hub 820. Catheter structures that are more distal are closer to the distal tip 805. Catheter structures that are more proximal are closer to the port 850. The distal end of the stylet electrode 860 is the distal tip 863. The proximal end of the stylet electrode 860 is the handle 861.

In one embodiment, when the electrode 860 is positions within the inner lumen of the catheter 890 and electrical signals are delivered to the electrode shaft 862 by connecting the electrode to an electrical signal generator via connector 840, contact between the electrode shaft 862 and the inner surfaces of the metallic coil 801, said electrical signals are conducted to the active tip 800 of the catheter 890 and thereby delivered to tissue in contact with the active tip 800. In one embodiment, the injection electrode system in FIG. 8 can be used in the embodiments presented in FIG. 1A and FIG. 1B. The injection electrode system can provide for radiofrequency therapy by means of catheter 890 placement in the spinal canal. The injection electrode system can provide epidural anesthesia. The injection electrode system can provide stimulation-guided RF and pulsed RF treatment of nervous structures, such as the DRG, via placement of the catheter 890 within the spinal canal. The injection electrode system can provide for stimulation-guided epidural anesthesia, such a lysis of adhesions. The injection electrode system can provide for temperature-monitoring of the catheter tip 800 during medical use.

The port 850 can be integrated inseparably into the hub 820. In one embodiment, the hub 820 and injection port 850 can be inseparably connected to the shaft 810. In another embodiment, a unitized hub 820 and injection port 850 can be separable from the shaft; for example. The unitized hub 820 and injection port 850 can take the form of a tuohy-borst adaptor or another common type of injection adaptor that is familiar to one skilled in the art of epidural anesthesia. The electrode can be moveable within the catheter. The electrode can be fully removed from the catheter. The electrode can be fully removed form the catheter to provide access to the injection port 850 for the injection of fluid through the catheter and outflowing from the catheter tip 800, for example, for the purpose of effective epidural anesthesia.

In some embodiments, the shaft 810 and tip 800 of the catheter 890 can have the same construction to the shaft and tip of electrodes presented in FIGS. 2, 3, 4, 5, 6, and 7. In one embodiment, the coil 801 can e a stainless steel spring coil of round wire. In one embodiment, the coil 801 can be a stainless steel spring coil of flat wire. In one embodiment, the coil 801 can be a laser cut stainless steel tube. It is understood that in other embodiments, the coil 801 is not present over the entire length of the shaft 810; for example, the proximal end of the coil 801 can be connected to meal tubing, such as stainless steel hypotube, to provide for a stiffer proximal part of the shaft. It is understood that multiple pieces of coil can be connected to form the coil 801. In some embodiments, the catheter electrode system presented in FIG. 8A and FIG. 8B has the same construction and function as the injection electrode system presented in FIG. 9A and FIG. 9B.

The electrode 890 can have constructions that are familiar to one skilled in the art of RF pain management. For example, electrode 890 can have a construction similar to that of the Cosman CSK electrode. For example, electrode 890 can have a construction similar to that of the Cosman TCD electrode. For example, electrode 890 can have a construction similar to that of the Cosman TCN electrode, whose shaft includes nitinol. The electrode 890 can be a temperature-sensing electrode. The electrode 890 can have a thermocouple temperature sensor at its distal 863. The electrode 860 can be configured to provide for the delivery of radiofrequency current to the catheter 890. The connector 840 can be configured to connect to a radiofrequency generator.

Referring to FIG. 8A and FIG. 8B, the catheter 890 can be an epidural catheter. The catheter 890 can be an intravascular catheter. The catheter 890 can be configured for epidural anesthesia. The stylet electrode 860 can be configured act as a stylet for the catheter 890. The stylet electrode 860 can be configured to deliver electrical signals to the active tip 800 of the catheter 890. The stylet electrode 860 can be configured to deliver RF signals to the active tip 800 of the catheter 890. The stylet electrode 860 can be configured to deliver nerve stimulation signals to the active tip 800 of the catheter 890. The injection electrode system presented in FIG. 8 can be configured to effect radiofrequency treatment, such as pulsed radiofrequency treatment, on nerve structures by means of placement of the electrode system in the epidural space of a human body. One advantage of the injection electrode system presented in FIG. 8 is that manufacture of the electrode 860 and the catheter 890 can proceed in parallel. Another advantage of the injection electrode system presented in FIG. 8 is that standard epidural methods can be used in addition to RF methods in the same medical procedure. Another advantage of the injection electrode system presented in FIG. 8 wherein the unitized hub 820 and injection port 850 is separable from shaft 810 of the catheter 890, is that the needle used to introduce the catheter 890 can be removed from the patient while the catheter 890 is in place within the patient, by sliding said needle over the distal end of the shaft 810, as is familiar one skilled in the art of epidural anesthesia.

Referring now specifically to FIG. 8B, in one embodiment of the injection electrode system, the catheter 890 has a safety strap 880 connected to the proximal end of the coil 801 at junction 884 and to the distal end of the coil 801 at junction 881. The junction 884 can be a weld, such as a laser weld. The junction 881 can be part of the weld, such as a laser weld or an electrical discharge weld, that forms the closed end 805 of the catheter 890. The safety strap 880 can be configured to prevent the coil 801 from uncoiling during use. The safety strap can be a metal wire. The safety strap can be a flat wire. The safety strap can be configured to have a low profile to allow entry of the stylet electrode's shaft 862 into the inner lumen of the coil 801. The safety strap can be configured to have a low profile to maintain an open cross-sectional area within the inner lumen of the coil for the flow of injected and aspirated fluid. In embodiments where the safety strap 880 is a metal wire, the safety strap can improve faithful conduction of electrical signals delivered by the electrode 860 to the active tip 800 of the catheter 890.

Referring to FIG. 8A and FIG. 8B, the length of the catheter 890 can be in the range 12-33 inches. The length of the catheter 890 can be less than 12 inches. The length of the catheter 890 can be greater than 33 inches. The length of the catheter 890 can be 12 inches. The length of the catheter 890 can 33 inches. The length of the catheter 890 can be 16 inches. The length of the catheter 890 can be 24 inches. The outer diameter of the catheter 890 can in the range 18 to 21 gauge. The outer diameter of the catheter 890 can be greater than 8 gauge. The outer diameter of the catheter 890 can be less than 21 gauge. The outer diameter of the catheter 890 can be 20 gauge. The outer diameter of the catheter 890 can be 19 gauge. The diameter of the electrode 860 can be configured to produce a desired stiffness of the assembled catheter shaft 810. The stiffness catheter shaft 810 and tip 800 can be configured to facilitate safe placement of the catheter 890 in the spinal canal. The introducer needle for the catheter can be 15 gauge. The introducer needle for the catheter can be 16 gauge. The introducer needle for the catheter can be 17 gauge. The introducer needle for the catheter can be 18 gauge. The introducer needle can be an epidural needle, such as a tuohy needle.

For embodiments where the hub 820 and injection port 850 are attached to the catheter shaft 810 (either separably as in the case where hub 820 and port 850 are an injection adaptor port, or inseparably as in the case where the hub 820 and port 850 are inseparable attached to the catheter shaft 810), the length of the electrode 860 can be configured so that when the electrode 860 is fully inserted into the catheter 890, the electrode's distal end 863 contacts the inner surface of the distal end 805 of the coil 801. One advantage of this configuration is that it provides tactile physical feedback the user that the electrode 860 is fully inserted in the catheter 890. For embodiments where the hub 820 and injection port 850 are attached to the catheter shaft 810 (either separably as in the case where hub 820 and port 850 are an injection adaptor port, or inseparably as in the case where the hub 820 and port 850 are inseparable attached to the catheter shaft 810), the length of the electrode 860 can be configured so that when the electrode 860 is fully inserted into the catheter 890, the electrode's distal end 863 cannot contact the inner surface of the distal end 805 of the coil 801. For example, as shown in FIG. 8B, the hub 861 of the electrode 860 can abut a surface of the port 850 to prevent further advancement of the electrode shaft 862 to the catheter shaft 810. One advantage of this configuration is that it ensures the distal end of the catheter 890 remains floppy irrespective of the position of the electrode 860 in the catheter 890. For embodiments where the hub 820 and injection port 850 are not attached to the catheter shaft 810 and the electrode 860 is inserted directly in the proximal end of the catheter shaft 810, the length of the electrode 860 can be configured so that when the electrode 860 is fully inserted into the catheter 890, the electrode's distal end 863 contacts the inner surface of the distal end 805 of the coil 801. One advantage of this configuration is that it provides tactile physical feedback the user that the electrode 860 is fully inserted in the catheter 890. For embodiments where the hub 820 and injection port 850 are not attached to the catheter shaft 810 and the electrode 860 is inserted directly in the proximal end of the catheter shaft 810, the length of the electrode 860 can be configured so that when the electrode 860 is fully inserted into the catheter 890, the electrode's distal end 863 cannot contact the inner surface of the distal end 805 of the coil 801. One advantage of this configuration is that it ensures the distal end of the catheter 890 remains floppy irrespective of the position of the electrode 860 in the catheter 890.

Figure 9A:
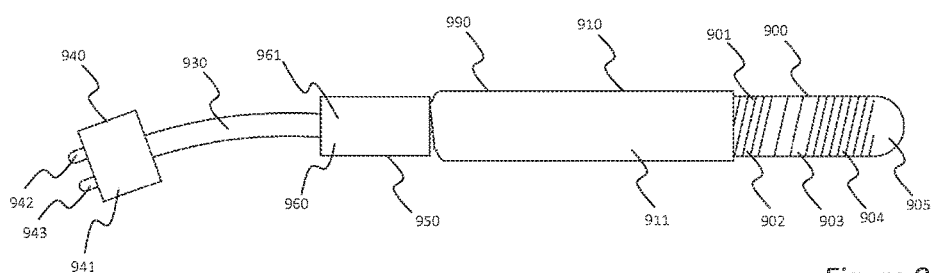
FIG. 9A is a schematic diagram showing in an external view an electrode system comprising a flexible catheter and stylet electrode.
Figure 9B:
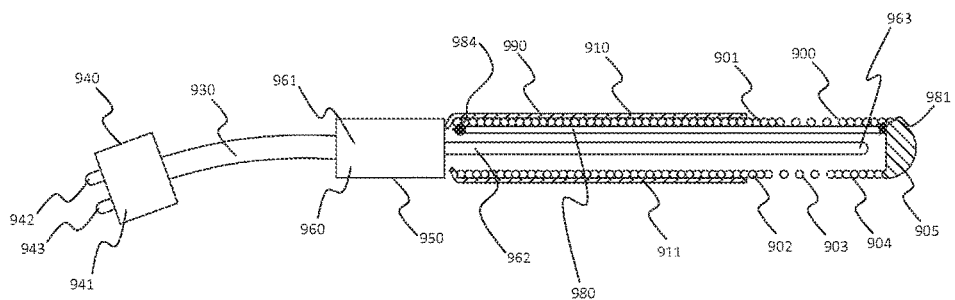
FIG. 9B is a schematic diagram showing in a sectional view an electrode system comprising a flexible catheter and stylet electrode.

FIG. 9 presents a catheter electrode system comprising a catheter 990 and separate, movable stylet electrode 960, in accordance with one aspect of the present invention. FIG. 9A presents one embodiment of the injection electrode system in an external view. FIG. 9B presents one embodiment of the internal construction of the injection electrode system, wherein the catheter 990 is shown in a cross-sectional view and the electrode 960 is shown from its exterior, positioned within the catheter 990. Referring to both FIG. 9A and FIG. 9B, the catheter 990 comprises a tip comprising coil 901 and distal end 905, shaft 910 comprising insulation 911 outside the coil 901. The electrode 960 comprises shaft 962, hub 960, cable 930, generator connector 940 comprising body 91 and pins 942 and 943. In some embodiments, the electrode 960 can be fully withdrawn from the catheter 990. The distal end of the catheter 990 is the end of the distal point 905, and the proximal end of the catheter 990 is end into which the electrode 960 can be inserted. Catheter structures that are more distal are closer to the distal tip 905. Catheter structures that are more proximal are closer to the end into which the electrode 960 can be inserted. The distal end of the stylet electrode 960 is the distal tip 963. The proximal end of the stylet electrode 960 is the handle 961.

In some embodiments, the catheter electrode system presented in FIG. 9A and FIG. 9B has the same construction and function as the injection electrode system presented in FIG. 8A and FIG. 8B. In some embodiments, the construction and function of the system presented in FIG. 9 is the same as that presented in FIG. 8 with the difference that the hub 820 and port 850 are not explicitly shown in FIG. 9. It is understood that in some embodiments, an injection adaptor, for instance a tuohy-borst adaptor or removable injection hub 820 and 850, can be attached to the proximal end of the catheter 990 to provide for injection of fluids. In one embodiment, the catheter 990 is an epidural catheter, familiar to one skilled in the art of epidural anesthesia. In one embodiment, the catheter 990 is an epidural catheter constructed using a metal coil. In one embodiment, the electrode 960 is a radiofrequency electrode configured to move through the inner lumen of the catheter 990. In one embodiment, the electrode 960 is configured to deliver electrical signals, such as radiofrequency, pulsed radiofrequency, and stimulation signals, to the active tip 900 of the catheter. In one embodiment, electrical signals delivered to the electrode 960 by connection of its generator connector 940 to an electrical generator, are in turn conducted to the active tip 900 of catheter 990 by contact between the electrode shaft 962 with the inner surface of the coil 901.

Referring now specifically to FIG. 9B, in one embodiment of the injection electrode system, the catheter 990 has a safety strap 980 connected to the proximal end of the coil 901 at junction 984 and to the distal end of the coil 901 at junction 981. The junction 984 can be a weld, such as a laser weld. The junction 981 can be a part of the weld, such as a laser weld or an electrical discharge weld, that forms the closed end 805 of the catheter 990. The safety strap 980 can be configured to prevent the coil 901 from uncoiling during use. The safety strap can be a metal wire. The safety strap can be a flat wire. The safety strap can be configured to have a low profile to allow entry of the stylet electrode's shaft 962 into the inner lumen of the coil 901. The safety strap can be configured to have a low profile to maintain an open cross-sectional area within the inner lumen of the coil for the flow of injected and aspirated fluid. In embodiments where the safety strap 980 is a metal wire, the safety strap can improve faithful conduction of electrical signals delivered by the electrode 960 to the active tip 900 of the catheter 990. In one embodiment, the electrode 960 can be long enough that its distal end 963 contacts the inner distal surface 905 of the catheter 990 when it is fully inserted into the catheter 990. In one embodiment, the electrode 960 is configured such that its distal end 963 does not contact the inner surface of the distal end 905 of the catheter 990, when the electrode 960 is fully inserted into the catheter 990. For example, as shown in FIG. 9B, the hub 961 of the electrode 960 can be constructed to abut the proximal end of the catheter 890 and thereby prevent the distal end 963 of the electrode shaft 962 from contacting the distal end of the inner lumen of the coil 901.

What is claimed:

1. A unitized injection electrode with a proximal and a distal end comprising the following inseparably connected elements: a metallic coil having a proximal end and a distal end; a metallic rod disposed within a lumen of the metallic coil and having a proximal end and a distal end; electrical insulation that covers the proximal end of the metallic coil and leaves the distal end of the metallic coil uninsulated; an injection port connected to the proximal end of the metallic coil and configured such that fluid injected into the port flows out of the uninsulated distal end of the metallic coil; and an electrical connector configured so that an electrical signal delivered to the electrical connector is delivered to tissue in contact with the uninsulated distal end of the metallic coil; wherein the proximal end of the metallic coil is directly attached to the metallic rod and wherein the distal end of end of the metallic coil is directly attached to the metallic rod.

2. The unitized injection electrode of in claim 1 wherein the electrical signal is a radiofrequency signal.

3. The unitized injection electrode of in claim 1 wherein the electrode is configured for placement in the epidural space.

4. The unitized injection electrode of in claim 1 wherein the distal end of the metallic coil is closed by a weld.

5. The unitized injection electrode of in claim 4 wherein the weld captures thermocouple wires to form a thermocouple temperature sensor, wherein the weld captures the distal end of the metallic rod, the proximal end of the metallic rod also being directly attached to the proximal end of the metallic coil, and wherein temperature signals from the temperature sensor can be measured by connection to a temperature connector that is inseparably attached to the electrode.

6. The unitized injection electrode of in claim 1 wherein the distal end of the metallic coil includes a temperature sensor.

7. The unitized injection electrode of in claim 6 wherein the electrical connector also includes connectors to the temperature sensor.

8. The unitized injection electrode of in claim 1 wherein the metallic coil is a stainless-steel coil.

9. The unitized injection electrode of in claim 1 wherein the metallic coil is a stainless-steel coil made from round wire.

10. The unitized injection electrode of in claim 1, wherein the distal end of the metallic rod is directly attached to the distal end of the metallic coil by a junction that comprises one or more of a weld joint, a glue joint, or a solder joint.

11. The unitized injection electrode of in claim 10, wherein the proximal end of the metallic rod is directly attached to the proximal end of the metallic coil by a junction that comprises one or more of a weld joint, a glue joint, or a solder joint.

12. The unitized injection electrode of in claim 1, wherein the distal end of the metallic rod is directly attached to the distal end of the metallic coil by a junction that comprises a weld joint.

13. The unitized injection electrode of in claim 12, wherein the proximal end of the metallic rod is directly attached to the proximal end of the metallic coil by a junction that comprises a weld joint.

14. The unitized injection electrode of in claim 12, wherein the proximal end of the metallic rod is directly attached to the proximal end of the metallic coil by a junction that comprises a solder joint.

15. The unitized injection electrode of in claim 1, wherein the proximal end of the metallic rod is directly attached to the proximal end of the metallic coil by a junction that comprises one or more of a weld joint, a glue joint, or a solder joint.

16. The unitized injection electrode of in claim 1, wherein the proximal end of the metallic rod is directly attached to the proximal end of the metallic coil by a junction that comprises a weld joint.

17. The unitized injection electrode of in claim 1, wherein the proximal end of the metallic rod is directly attached to the proximal end of the metallic coil by a junction that comprises a solder joint.

* * * * *